United States Patent
Crooks et al.

(10) Patent No.: US 7,368,443 B2
(45) Date of Patent: *May 6, 2008

(54) 2,6-DISUBSTITUTED PIPERIDINES AND PIPERAZINE COMPOUNDS

(75) Inventors: Peter A. Crooks, Nicholasville, KY (US); Linda Dwoskin, Lexington, KY (US); Marlon D. Jones, Compton, CA (US); Dennis Keith Miller, Columbia, MO (US); Seth Davin Norholm, Atlanta, GA (US); Guangrong Zheng, Lexington, KY (US); Sairam Krishamurthy, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 279 days.

This patent is subject to a terminal disclaimer.

(21) Appl. No.: 10/813,647

(22) Filed: Mar. 31, 2004

(65) Prior Publication Data

US 2004/0266824 A1 Dec. 30, 2004

Related U.S. Application Data

(60) Continuation-in-part of application No. 10/231,156, filed on Aug. 30, 2002, now Pat. No. 6,943,177, which is a division of application No. 09/628,557, filed on Jul. 28, 2000, now Pat. No. 6,455,543.

(60) Provisional application No. 60/146,144, filed on Jul. 30, 1999.

(51) Int. Cl.
*A61K 31/445* (2006.01)
*C07D 211/20* (2006.01)

(52) U.S. Cl. ............ 514/183; 514/317; 514/327; 514/329; 514/330; 514/331; 540/450; 540/482; 540/484; 540/609; 540/612; 546/192; 546/216; 546/220; 546/221; 546/223; 546/224; 546/225; 546/227; 546/229; 546/232

(58) Field of Classification Search ............ 514/183, 514/317, 327, 329, 330, 331; 540/450, 482, 540/484, 609, 612; 546/192, 216, 220, 221, 546/223, 224, 225, 227, 229, 232
See application file for complete search history.

(56) References Cited

U.S. PATENT DOCUMENTS 5,414,005 A  5/1995 Schneider et al.
5,486,362 A  1/1996 Kitchell et al.
5,830,904 A  11/1998 Crooks et al.
6,087,376 A  7/2000 Crooks et al.
6,455,543 B1  9/2002 Dwoskin et al.
6,703,406 B2  3/2004 Crooks et al.

FOREIGN PATENT DOCUMENTS

FR  2 528 834  6/1982
WO  WO 01/08678 A1  2/2001

OTHER PUBLICATIONS

Flammia et al, Journal of Medicinial Chemistry, vol. 42, No. 18, pp. 3726-3731, 1999.*
Database CAS on STN, (Columbus, OH, USA) Accession No. 103:88116 "Lobelanine" CS217195, (1982).
Database CAS on STN, (Columbus, OH, USA) Accession No. 123:37615 Schiffrin et al. "Electroassisted separation of metals by solvent extraction and supported-liquid memberanes", HYDROMETALL. '94, Int. symp. (1994).
Database CAS on STN, (Columbus, OH, USA) Accession No. 66:22229, Kracmar et al. "Ultraviolet spectrophotometry in the control of drugs" Pharmazie (1966).
Database CAS on STN, (Columbus, OH, USA) Accession No. 72:65748, Schoenenberger et al. "Action mechanism of antimicrobial beta-amino ketones", Phar. Acta helv.(1996) vol. 44, No. 11, pp. 691-714.
Database CAS on STN, (Columbus, OH, USA) Accession No. 128:270483, Katritzky et al. "A short asymmetric synthesis of 2,5-disubstituted pyrrolidines", Tetrahedron Lett (1998) vol. 39, pp. 1698-1700.
The Condensed Chemical Dictionary 1956 Fifth Edition p. 110.

* cited by examiner

*Primary Examiner*—Zinna N. Davis
(74) *Attorney, Agent, or Firm*—McDermott Will & Emery LLP

(57) ABSTRACT

The present invention is directed to 2,6-disubstituted piperidine and piperazine analogs having the following general formula:

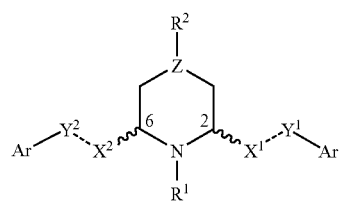

which are used to treat diseases of the central nervous system, drug abuse, and withdrawal therefrom as well as treating eating disorders.

19 Claims, No Drawings

2,6-DISUBSTITUTED PIPERIDINES AND PIPERAZINE COMPOUNDS

This application is a continuation-in-part of application Ser. No. 10/231,156 filed Aug. 30, 2002, now U.S. Pat. No. 6,943,177 which in turn is a divisional of application Ser. No. 09/628,557 filed Jul. 28, 2000, now U.S. Pat. No. 6,455,543 B1, which in turn claims priority under 35 U.S.C. § 119(e)(1) to provisional Application No. 60/146,144 filed Jul. 30, 1999, all of which is incorporated herein by reference.

FIELD OF INVENTION

The present invention relates to lobeline analogs, i.e., 2,6-disubstituted piperidine, and 2,6-disubstituted piperazine compounds, and their method of use in the treatment of diseases and pathologies of the central nervous system (CNS), the treatment of drug abuse and withdrawal therefrom as well as to the treatment of eating disorders such as obesity. The 2,6-disubstituted piperidine and piperazine compounds of the present invention can be used for the treatment of drug abuse and withdrawal therefrom, as well as for the treatment of eating disorders such as obesity, and other neuropathologies.

BACKGROUND OF THE INVENTION

Alpha-Lobeline (lobeline), a lipophilic nonpyridino, alkaloidal constituent of Indian tobacco, is a major alkaloid in a family of structurally-related compounds found in *Lobelia inflata*. Lobeline has been reported to have many nicotine like effects, including tachycardia and hypertension (Olin et al., 1995), hyperalgesia (Hamann et al., 1994) and improvement of learning and memory (Decker et al., 1993). Lobeline has high affinity for nicotinic receptors (Lippiello et al., 1986; Broussolle et al., 1989). However, no obvious structural resemblance of lobeline to nicotine is apparent and structure function relationships between S(−)-nicotine and lobeline do not suggest a common pharmacophore (Barlow et al., 1989). Also, differential effects of lobeline and nicotine suggest that these drugs may not be active through a common CNS mechanism, even though lobeline has been considered a mixed nicotinic agonist/antagonist.

Lobeline evokes dopamine (DA) release from rat striatal slices. However, lobeline evoked DA release is neither dependent upon extracellular calcium nor is it sensitive to mecamylamine, a noncompetitive nicotinic receptor antagonist. Thus, lobeline evoked DA release occurs via a different mechanism than does nicotine to evoke DA release (Teng et al., 1997, 1998; Clarke et al., 1996). In this respect, lobeline also inhibits DA uptake into rat striatal synaptic vesicles via an interaction with the dihydrotetrabenazine (DTBZ) site on vesicular monoamine transporter-2 (VMAT2), thus increasing the cytosolic DA available for reverse transport by the plasma membrane transporter (DAT) (Teng et al., 1997, 1998). Thus, lobeline interacts with nicotinic receptors and blocks nicotine-evoked DA release, but also interacts with DA transporter proteins (DAT and VMAT2) to modify the concentration of DA in the cytosolic and vesicular storage pools, thereby altering subsequent dopaminergic neurotransmission.

Currently, drug discovery is focusing on neuronal nicotinic receptors (nAChRs) as novel targets for the development of therapeutic agents for a wide variety of central nervous system (CNS) diseases including, drug addiction, neuroendocrine, neuropsychiatric and neurological diseases, memory and learning disabilities, eating disorders, and the control of pain, as well as cardiovascular and gastrointestinal disorders. Nicotinic receptor antagonists have good potential as therapeutic agents, since they offer another means of modulating nicotinic receptor function. Nicotinic agonists rapidly desensitize these receptors, essentially inhibiting their function. Thus, inhibition of nicotinic receptor function may be the action, which confers clinical utility, indicating that nicotinic receptor antagonists could also be beneficial in the treatment of diseases for which nicotinic agonists are currently being developed. For example, schizophrenia and drug abuse have both been associated with hyperactivity of CNS dopaminergic systems, and inhibition of nicotinic receptors may be advantageous in reducing such hyperactivity. Furthermore, the availability of subtype-selective nicotinic receptor antagonists will be invaluable agents in both basic and clinical research, with regard to both the treatment and diagnosis of disease. Finally, subtype-selective antagonists will define the role of specific nicotinic receptor subtypes in both physiological function and disease states.

The action of many neuropharmacologically therapeutic agents involve the modulation of dopamine (DA), norepinephrine (NE) and serotonin (5-HT) release, uptake and storage within its respective terminals in the central nervous system (CNS). Most neurotransmitters are stored in synaptic vesicles, which are prominent features of nerve terminals. Concentration into vesicles appears to be responsible for maintaining a ready supply of neurotransmitter available for neuronal exocytotic release into the synaptic cleft. Vesicles also serve the role of protecting the neurotransmitter from metabolic breakdown. One transport site on the vesicle membrane is the vesicular monoamine transporter-2 (VMAT2), whose role is to transport transmitter from the cytosol into the synaptic vesicle. Dihydrotetrabenazine (DTBZ), a ligand structurally related to methoxytetrabenazine (MTBZ), has been used as a radiolabel to probe the interaction of drugs with VMAT2. Both DTBZ and MTBZ act at the same site on VMAT2. Once the neurotransmitter is released from the terminal into the synaptic space, it interacts with postsynaptic receptors and subsequently is taken back up into the terminal via the plasma membrane transporter (e.g., the dopamine transporter [DAT] and/or the serotonin transporter [SERT]). Thus, transporter proteins modify the concentration of neurotransmitter in the cytosolic and vesicular storage pools, thereby having the ability to alter subsequent neurotransmission.

SUMMARY OF THE INVENTION

The present invention is directed to a method of treating an individual who suffers from an eating disorder, from a disease or pathology of the central nervous system (CNS) or for treating an individual for drug dependence or withdrawal for drug dependence. The method comprises the step of administering to the individual an effective amount of a 2,6-disubstituted piperidine or piperazine lobeline analog, including pharmaceutically acceptable salts of such compounds thereof. As used herein, an "effective amount" refers to an amount of a drug effective to reduce an individual's desire for a drug of abuse or for food, or for alleviating at least one of the symptoms of the disease or pathological symptom of a CNS pathology.

The compound can be administered alone, combined with an excipient, or co-administered with a second drug having a similar or synergistic effect. The compound is administered subcutaneously, intramuscularly, intravenously, transdermally, orally, intranasally, intrapulmonary or rectally. The 2,6-disubstituted piperdine and piperazine analogs thereof in treating diseases or pathologies of the CNS is implicated. In particular, the treatment of dependencies on such drugs as cocaine, amphetamines, caffeine, nicotine, phencyclidine, opiates, barbiturates, benzodiazepines, cannabinoids, hallucinogens, and alcohol is implicated. Also, the treatment of eating disorders such as obesity is implicated.

In a preferred aspect of the invention, the method of treatment reduces an individual's desire for the drug of abuse or for food by at least one day, but it is also preferred that the treatment method further comprises administering behavior modification counseling to the individual. Although the compound of the present invention is contemplated primarily for the treatment of drug abuse and withdrawal and for eating disorders, other uses are also suggested by the studies discussed herein. Thus, cognitive disorders, brain trauma, memory loss, psychosis, sleep disorders, obsessive compulsive disorders, panic disorders, myasthenia gravis, Parkinson's disease, Alzheimer's disease, schizophrenia, Tourette's syndrome, Huntington's disease, attention deficit disorder, hyperkinetic syndrome, chronic nervous exhaustion, narcolepsy, pain, motion sickness and depression, and related conditions are considered to be susceptible to treatment with a compound of the present invention.

As shown by the results of the studies described herein, lobeline analogs are found to be effective in inhibiting uptake of extracellular DA by cells of the CNS. Some of these analogs are also nicotinic receptor antagonists. Either or both mechanisms can thereby work to alter the distribution of the intracellular DA pools and as a result alter extracellular DA concentration.

Further as shown by the results of the studies described herein, the 2,6-disubstituted piperidine analogs are found to be effective in inhibiting uptake of extracellular 5-HT by serotonergic nerve terminals in the CNS, as well as in inhibiting the binding of [$^3$H]MTBZ or [$^3$H]DTBZ to vesicle membranes indicating an interaction with VMAT2. These analogs are also nicotinic receptor antagonists, inhibiting nicotine-evoked [$^3$H]DA and [$^3$H]NE release from rat brain slices. Either or both mechanisms can thereby alter the distribution of the intracellular neurotransmitter pools, and as a result, alter extracellular neurotransmitter concentrations.

As used herein the term "lobeline" refers to a compound having the general chemical formula 2-[6-(β-hydroxyphenethyl)-1-methyl-2-piperidyl]-acetophenone. The term "lobeline analogs" and equivalents thereof as used herein, refers to chemical derivatives of lobeline obtained by oxidation or reduction of lobeline, others obtained by esterification of lobeline and redox derivatives, as well as various substitutions at the N-position of the piperidinyl moiety, different substituents at the piperidinyl C2 and C6 positions, compounds with different combinations of chiralities at positions 2 and 6 on the piperidinyl ring, aza analogs at the C4 position of the piperidinyl ring, a variety of aryl moieties replacing the two phenyl moieties, and a variety of substituents in one or more of the aryl moieties.

DETAILED DESCRIPTION OF THE INVENTION

The 2,6-disubstituted piperidine and piperazine analogs of the present invention include those contemplated by the following formula (I), without regard to chirality:

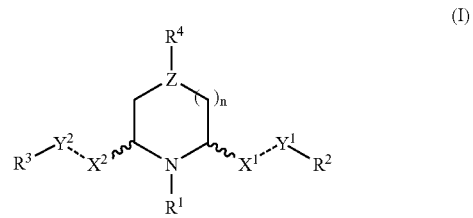

wherein:

n is zero or an integer in the range from 1 to 3;

$X^1$—$Y^1$ and $X^2$—$Y^2$ are the same or are independently different from one another and represent a saturated carbon-carbon bond, a cis-carbon-carbon double bond, a trans-carbon-carbon double bond, a carbon-carbon triple bond; a saturated sulfur-carbon bond, a saturated selenium-carbon bond, an oxygen-carbon bond, a saturated nitrogen-carbon bond, a N-alkyl substituted saturated nitrogen-carbon bond where said alkyl is a lower straight chain or branched alkyl, a nitrogen-carbon double bond, or a nitrogen-nitrogen double bond;

Z-$R^4$ represents N—$R^4$, CH—$R^4$ or C=O, where $R^4$ is hydrogen or a lower straight chain or branched alkyl;

$R^1$ represent hydrogen or a lower straight chain or branched alkyl, cycloalkyl, vinyl, allyl, alkenyl (including cis and trans geometrical forms), benzyl, and phenylethyl, or, when Z is CH—$R^4$, $R^1$ and $R^4$ together form a ring including a —$CH_2$—, —O—$CH_2$—O—, —$CH_2CH_2$—, —$CH_2CH_2$—$CH_2$—, -cis-CH=CH, -cis-$CH_2$—CH=CH— or -cis-$CH_2$=CH—$CH_2$— moiety; and $R^2$ and $R^3$ are the same or are independently different from one another and represent a saturated or unsaturated hydrocarbon ring; a nitrogen containing heterocyclic moiety; an oxygen containing heterocyclic moiety; a sulfur containing heterocyclic moiety; a selenium containing heterocyclic moiety; a mixed heterocyclic moiety containing at least two atoms selected from the group consisting of nitrogen, oxygen and sulfur; and an ortho, meta or para-substituted benzene.

The substituted benzene of formula (I) is a substituted phenyl wherein the substituent moiety is a methyl, ethyl, propyl, isopropyl, butyl, sec-butyl isobutyl, $C_5$-$C_7$ straight chain or branched alkyl, $C_3$-$C_6$ cycloalkyl, $C_4$-$C_7$ alkenyl (including cis and trans geometrical forms), benzyl, and phenylethyl. Further, the substitute moieties can be amino, N-methylamino, N,N-dimethylamino, carboxylate, methylcarboxylate, ethylcarboxylate, propylcarboxylate, isopropylcarboxylate, carboxaldehyde, acetoxy, propionyloxy, isopropionyloxy, cyano, aminomethyl, N-methylaminomethyl, N,N-dimethylaminomethyl, carboxamide, N-methylcarboxamide, N,N-dimethylcarboxamide, acetyl, propionyl, formyl, benzoyl sulfate, phenyl, methylsulfate, hydroxyl, methoxy, ethoxy, propoxy, isopropoxy, thiol, methylthio, ethylthio, propiothiol, fluoro, chloro, bromo, iodo, trifluoromethyl, vinyl, allyl, propargyl, nitro, carbamoyl, ureido, azido, isocyanate, thioisocyanate, hydroxylamino and nitroso.

It is preferred that when either $X^1$—$Y^1$ or $X^2$—$Y^2$ is a saturated carbon-carbon bond, $Y^1$ or $Y^2$ represents $CH_2$, CH—OH, CHO-alkyl where said alkyl is a lower straight chain or branched alkyl, CH—$OSO_2$—$C_6H_5$, CH—$OSO_2$-p-$C_6H_4CH_3$, CH—SH, $C_6H_5$—SH, CH—S-alkyl where said alkyl is a lower straight chain or branched alkyl, CH—$NO_2$, CH—CF$_3$, CH—NHOH, CH—OCHO, CH—F, CH—Cl, CH—Br, CH—I, CH—NH$_2$, CH—NH-alkyl where said alkyl is a lower straight chain or branched alkyl, CH—N(alkyl)$_2$ where said alkyl is a lower straight chain or branched alkyl, CH—OCONH$_2$, CH—OCONH-alkyl where said alkyl is a lower straight chain or branched alkyl, CH—OCON(alkyl)$_2$ where said alkyl is a lower straight chain or branched alkyl, CH—N$_3$, C=O or C=S; CH—O-aryl such as a phenyl, ortho-, meta-, or para-substituted phenyl where the substituent is as described above; or a hydrocarbon or hetercyclic ring such as pyridyl, furanyl, naphthyl, thiazole, selenothenyl, oxazolyl, 1,2,3-triazole, 1,2,4-triazole, imidazoline, pyrimidine, pyridazine or triazine, including all possible substitution patterns, diastereomeric and enantiomeric forms thereof.

The lower straight or branched alkyl can be an alkyl group containing one to seven carbon atoms, with methyl and ethyl being preferred. R$^1$ represents a hydrogen, methyl, deuteromethyl (CD$_3$), tritiomethyl (CT$_3$), ethyl, or C$_3$-C$_7$ straight chain or branched alkyl (preferably methyl or ethyl), C$_3$-C$_6$ cycloalkyl, vinyl, allyl, C$_4$-C$_7$ alkenyl (including cis and trans geometrical forms), benzyl, and phenylethyl.

The above 2,6-substituted piperidino or piperazino analogs are preferred in their cis-geometrical isomeric forms, or in their trans geometric forms, including all possible geometric, racemic, diasteriomeric, and enantiomeric forms thereof.

The above 2,6-disubstituted piperidines or piperazines as well as analogs thereof can be administered in their free base form or as a soluble salt. Whenever it is desired to employ a salt of a 2,6-substituted piperidine or its analog, it is preferred that a soluble salt be employed. Some preferred salts include hydrochloride, hydrobromide, nitrate, sulfate, phosphate, tartrate, galactarate, fumarate, citrate, maleate, glycolate, malate, ascorbate, lactate, aspartate, glutamate, methanesulfonate, p-toluenesulfonate, benzenesulfonate, salicylate, proprionate, and succinate salts. The above salt forms may be in some cases hydrates or solvates with alcohols and other solvents.

In one embodiment, when n=0, R$^2$ and R$^3$ are unsubstituted phenyl groups, and X$^1$—Y$^1$ and X$^2$—Y$^2$ are saturated carbon-carbon bonds, Y$^1$ cannot be CH$_2$, CHOH or C=O, and Y$^2$ cannot be CH$_2$, CHOH, or C=O.

In another embodiment, when R$^2$ and/or R$^3$ is a saturated hydrocarbon ring, the ring includes, but is not limited to, cyclobutane, cyclopentane, cyclohexane, cycloheptane or cyclooctane, including all possible substitution patterns, geometric and stereoisomers, racemic, diastereomeric and enantiomeric forms thereof.

In still a further embodiment, when R$^2$ and/or R$^3$ is an unsaturated hydrocarbon ring, the ring includes, but is not limited to, benzene, cyclopentene, cyclohexene, cycloheptene, cyclooctene, cyclopentadiene, or napthylene, including all possible substitution patterns, geometric and stereoisomers, racemic, diastereomeric and enantiomeric forms thereof.

In still another embodiment, when R$^2$ and/or R$^3$ is a nitrogen containing heterocyclic moiety, the moiety includes, but is not limited to, azetine, piperidine, piperazine, pyrazine, pyrazole, pyrazolidine, imidazole imidazoline, pyrimidine, hexa-hydropyrimidine, pyrrole, pyrrolidine, triazine, 1,2,3-triazole, 1,2,4-triazole, pyridine or pyridazine, including all possible substitution patterns, geometric and stereoisomers, racemic, diastereomeric and enantiomeric forms thereof.

In still a further embodiment, when R$^2$ and/or R$^3$ is an oxygen containing heterocyclic moiety, the moiety includes, but is not limited to, furan, tetrahydrofuran, 2,5-dihydrofuran, pyran, tetrahydropyran, 1,4-dioxane, 1,3-dioxane or 1,4-oxathinin, including all possible substitution patterns, geometric and stereoisomers, racemic, diastereomeric and enantiomeric forms thereof.

In still a further embodiment, when R$^2$ and/or R$^3$ is a sulfur containing heterocyclic moiety, the moiety includes, but is not limited to, thietane, thiophene, thiophane, 2,5-dihydrothiophene, 1,3-dithiolylium, 1,3-dithiolane, 1,2-dithiolylium, 1,2-dithiolane, thiane, 1,2-dithiane, 1,3-dithane, 1,4-dithiane, or thiopyranylium, including all possible substitution patterns, geometric and stereoisomers, racemic, diastereomeric and enantiomeric forms thereof.

In still a further embodiment, when R$^2$ and/or R$^3$ is a selenium containing heterocyclic moiety, the moiety includes, but is not limited to, selenophene, including all possible substitution patterns, geometric and stereoisomers, racemic, diastereomeric and enantiomeric forms thereof.

In still a further embodiment, when R$^2$ and/or R$^3$ is a mixed heterocyclic moiety, the moiety includes, but is not limited to, thiazolidine, thiazole and oxazin, including all possible substitution patterns, geometric and stereoisomers, racemic, diastereomeric and enantiomeric forms thereof.

Still another embodiment is a 2,6-disubstituted piperdine analog having the following formula (II):

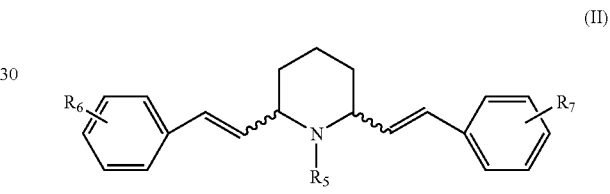

(II)

wherein

R$^5$ represents a hydrogen, methyl, deuteromethyl (CD$_3$), tritiomethyl (CT$_3$), ethyl, or C$_3$-C$_7$ straight chain or branched alkyl (preferably methyl or ethyl), C$_3$-C$_6$ cycloalkyl, vinyl, allyl, C$_4$-C$_7$ alkenyl (including cis and trans geometrical forms), benzyl, and phenylethyl; and R$^6$ and R$^7$ are substituted phenyls, each independently ortho-, meta-, or para-substituted moieties, where the substituent is described as hydrogen, methyl, ethyl, or C$_3$-C$_7$ straight chain or branched alkyl, C$_3$-C$_6$ cycloalkyl, vinyl, allyl, C$_4$-C$_7$ alkenyl (including cis and trans geometrical forms), benzyl, and phenylethyl. Further, the substitute moieties can be N-methylamino, N,N-dimethylamino, carboxylate, methylcarboxylate, ethylcarboxylate, propylcarboxylate, isopropylcarboxylate, carboxaldehyde, acetoxy, propionyloxy, isopropionyloxy, cyano, aminomethyl, N-methylaminomethyl, N,N-dimethylaminomethyl, carboxamide, N-methylcarboxamide, N,N-dimethylcarboxamide, acetyl, propionyl, formyl, benzoyl, sulfate, methylsulfate, hydroxyl, methoxy, ethoxy, propoxy, isopropoxy, thiol, methylthio, ethylthio, propiothiol, fluoro, chloro, bromo, iodo, trifluoromethyl, propargyl, nitro, carbamoyl, ureido, azido, isocyanate, thioisocyanate, hydroxylamino, and nitroso.

The above 2,6-substituted piperidino analogs for formulas (I) and (II) are preferred in their 2,6-cis geometrical isomeric forms, or in their 2,6-trans geometric forms, including all possible geometric, racemic, diasteriomeric, and enantiomeric forms thereof.

A pharmaceutical composition containing a compound of the invention is also contemplated, which may include a conventional additive, such as a stabilizer, buffer, salt, preservative, filler, flavor enhancer and the like, as known to those skilled in the art. Representative buffers include phosphates, carbonates, citrates and the like. Exemplary preservatives include EDTA, EGTA, BHA, BHT and the like. A composition of the invention may be administered by inhalation, i.e., intranasally as an aerosol or nasal formulation; topically, i.e., in the form of an ointment, cream or lotion; orally, i.e., in solid or liquid form (tablet, gel cap, time release capsule, powder, solution, or suspension in aqueous or non aqueous liquid; intravenously as an infusion or injection, i.e., as a solution, suspension or emulsion in a pharmaceutically acceptable carrier; transdermally, e.g., via a transdermal patch; rectally as a suppository and the like.

Generally, the pharmacologically effective dose of a present compound is in the amount ranging from about $1 \times 10^{-5}$ to about 1 mg/kg body weight/day. The amount to be administered depends to some extent on the lipophilicity of the specific compound selected, since it is expected that this property of the compound will cause it to partition into fat deposits of the subject. The precise amount to be administered can be determined by the skilled practitioner in view of desired dosages, side effects and medical history of the patient and the like.

The 2,6-disubstituted piperidino and piperazino analogs of the present invention exhibit selectivity for either neuronal nicotinic acetylcholine receptors (nAChRs) and/or the dopamine transporter protein (DAT) and/or the serotonin transporter protein (SERT) and/or the norepinephrine transporter (NET) and/or the vesicular monoamine transporter (VMAT2).

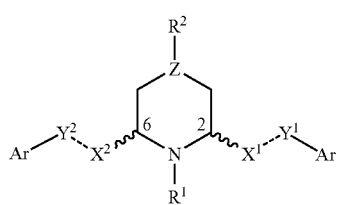

(III)

Compound
1. 2R, 6S, $X^1=X^2=CH_2$, $Y^1=C=O$, $Y^2=(S)$—CHOH, Z=CH, $R^1=CH_3$, $R^2=H$, Ar=Ph
2. 2R, 6S, $X^1=X^2=CH_2$, $Y^1=C=O$, $Y^2=(S)$—CHOSO$_2$—C$_6$H$_4$-p-CH$_3$, Z=CH, $R^1=CH_3$, $R^2=H$, Ar=Ph
3. 2, 6-cis, $X^1=X^2=CH_2$, $Y^1=Y^2=C=O$, Z=CH, $R^1=CH_3$, $R^2=H$, Ar=Ph
4. 2R, 6S, $X^1=X^2=CH_2$, $Y^1=(R)$—CHOH, $Y^2=(S)$—CHOH, Z=CH, $R^1=CH_3$, $R^2=H$, Ar=Ph
5. 2R, 6S, $X^1=CH_2$, $Y^1=C=O$, $X^2$, $Y^2=$trans CH=CH, Z=CH, $R_1=CH_3$, $R^2=H$, Ar=Ph
6. 2R, 6S, $X^1=CH_2$, $Y^1=(R)$—CHOH, $X^2$, $Y^2=$trans CH=CH, Z=CH, $R^1=CH_3$, $R^2=H$, Ar=Ph
7. 2R, 6S, $X^1=CH_2$, $Y^1=(S)$—CHOH, $X^2$, $Y^2=$trans CH=CH, Z=CH, $R^1=CH_3$, $R_2=H$, Ar=Ph
8. 2R, 6S, $X^1$, $Y^1=$trans CH=CH, $X^2=CH_2$, $Y^2=(S)$—CHOH, Z=CH, $R^1=CH_3$, $R^2=H$, Ar=Ph
9. 2R, 6S, $X^1$, $Y^1=$trans CH=CH, $X^2=CH_2$, $Y^2=(R)$—CHOH, Z=CH, $R^1=CH_3$, $R^2=H$, Ar=Ph
10. 2R, 6S, $X^1=X^2=Y^2=CH_2$, $Y^1=(R)$—CHOH, Z=CH, $R^1=CH_3$, $R^2=H$, Ar=Ph
11. 2R, 6S, $X^1=X^2=Y^2=CH_2$, $Y^1=(S)$—CHOH, Z=CH, $R^1=CH_3$, $R^2=H$, Ar=Ph
12. 2R, 6S, $X^1=X^2=Y^1=CH_2$, $Y^2=(S)$—CHOH, Z=CH, $R^1=CH_3$, $R^2=H$, Ar=Ph
13. 2R, 6S, $X^1=X^2=Y^1=CH_2$, $Y^2=(R)$—CHOH, Z=CH, $R^1=CH_3$, $R^2=H$, Ar=Ph
14. 2, 6-cis, $X^1$, $Y^1=$trans CH=CH, $X^2$, $Y^2=$trans CH=CH, Z=CH, $R^1=CH_3$, $R^2=H$, Ar=Ph
15. 2S, 6S, $X^1$, $Y^1=$trans CH=CH, $X^2$, $Y^2=$trans CH=CH, Z=CH, $R^1=CH_3$, $R^2=H$, Ar=Ph
16. 2R, 6R, $X^1$, $Y^1=$trans CH=CH, $X^2$, $Y^2=$trans CH=CH, Z=CH, $R^1=CH_3$, $R^2=H$, Ar=Ph
17. 2, 6-cis, $X^1=X^2=Y^1=Y^2=CH_2$, Z=CH, $R^1=CH_3$, $R^2=H$, Ar=Ph
18. 2S, 6S, $X^1=X^2=Y^1=Y^2=CH_2$, Z=CH, $R^1=CH_3$, $R^2=H$, Ar=Ph
19. 2S, 6R, $X^1=X^2=Y^1=Y^2=CH_2$, Z=CH, $R^1=CH_3$, $R^2=H$, Ar=Ph
20. 2R, 6S, $X^1=Y^1=CH_2$, $X^2$, $Y^2=$trans CH=CH, Z=CH, $R^1=CH_3$, $R^2=H$, Ar=Ph
21. 2R, 6S, $X^1$, $Y^1=$trans CH=CH, $X^2=Y^2=CH_2$, Z=CH, $R^1=CH_3$, $R^2=H$, Ar=Ph
22. 2S, 6S, $X^1$, $Y^1=$trans CH=CH, $X^2=Y^2=CH_2$, Z=CH, $R^1=CH_3$, $R^2=H$, Ar=Ph
23. 2,6-trans, $X^1$, $Y^1=$trans CH=CH, $X^2$, $Y^2=$trans CH=CH, Z=CH, $R^1=H_3$, $R^2=H$, Ar=Ph
24. 2,6-trans, $X^1$, $Y^1=$trans CH=CH, $X^2$, $Y^2=$trans CH=CH, Z=CH, $R^1=H_3$, $R^2=H$, Ar=Ph
25. 2,6-cis, $X^1=X^2=Y^1=Y^2=CH_2$, Z=CH, $R^1=H$, $R^2=H$, Ar=Ph
26. 2,6-cis, $X^1=X^2=Y^1=Y^2=CH_2$, Z=CH, $R^1=CH_2CH_3$, $R^2=H$, Ar=Ph
27. 2,6-cis, $X^1=X^2=Y^1=Y^2=CH_2$, Z=CH, $R^1=CH_2CH_2CH_3$, $R^2=H$, Ar=Ph
28. 2,6-cis, $X^1=X^2=Y^1=Y^2=CH_2$, Z=CH, $R^1=H$, $R^2=H$, Ar=3,4-(O—CH$_2$—O)-Ph
29. 2,6-cis, $X^1=X^2=Y^1=Y^2=CH_2$, Z=CH, $R^1=CH_3$, $R^2=H$, Ar=3,4-(O—CH$_2$—O)-Ph
30. 2,6-cis, $X^1=X^2=Y^1=Y^2=CH_2$, Z=CH, $R^1=H$, $R^2=H$, Ar=2-F-Ph
31. 2,6-cis, $X^1=X^2=Y^1=Y^2=CH_2$, Z=CH, $R^1=CH_3$, $R^2=H$, Ar=2-F-Ph
32. 2,6-cis, $X^1=X^2=Y^1=Y^2=CH_2$, Z=CH, $R^1=H$, $R^2=H$, Ar=3-F-Ph
33. 2,6-cis, $X^1=X^2=Y^1=Y^2=CH_2$, Z=CH, $R^1=CH_3$, $R^2=H$, Ar=3-F-Ph
34. 2,6-cis, $X^1=X^2=Y^1=Y^2=CH_2$, Z=CH, $R^1=H$, $R^2=H$, Ar=4-F-Ph
35. 2,6-cis, $X^1=X^2=Y^1=Y^2=CH_2$, Z=CH, $R^1=CH_3$, $R^2=H$, Ar=4-F-Ph
36. 2,6-cis, $X^1=X^2=Y^1=Y^2=CH_2$, Z=CH, $R^1=H$, $R^2=H$, Ar=2-MeO-Ph
37. 2,6-cis, $X^1=X^2=Y^1=Y^2=CH_2$, Z=CH, $R^1=CH_3$, $R^2=H$, Ar=2-MeO-Ph
38. 2,6-cis, $X^1=X^2=Y^1=Y^2=CH_2$, Z=CH, $R^1=H$, $R^2=H$, Ar=3-MeO-Ph
39. 2,6-cis, $X^1=X^2=Y^1=Y^2=CH_2$, Z=CH, $R^1=CH_3$, $R^2=H$, Ar=3-MeO-Ph
40. 2,6-cis, $X^1=X^2=Y^1=Y^2=CH_2$, Z=CH, $R^1=H$, $R^2=H$, Ar=4-MeO-Ph
41. 2,6-cis, $X^1=X^2=Y^1=Y^2=CH_2$, Z=CH, $R^1=CH_3$, $R^2=H$, Ar=4-MeO-Ph
42. 2,6-cis, $X^1=X^2=Y^1=Y^2=CH_2$, Z=CH, $R^1=H$, $R^2=H$, Ar=4-Me-Ph
43. 2,6-cis, $X^1=X^2=Y^1=Y^2=CH_2$, Z=CH, $R^1=CH_3$, $R^2=H$, Ar=4-Me-Ph 44. 2,6-cis, $X^1=X^2=Y^1=Y^2=CH_2$, Z=CH, $R^1=H$, $R^2=H$, Ar=3-CF$_3$-Ph
45. 2,6-cis, $X^1=X^2=Y^1=Y^2=CH_2$, Z=CH, $R^1=CH_3$, $R^2=H$, Ar=3-CF$_3$-Ph
46. 2,6-cis, $X^1=X^2=Y^1=Y^2=CH_2$, Z=CH, $R^1=H$, $R^2=H$, Ar=4-Ph-Ph
47. 2,6-cis, $X^1=X^2=Y^1=Y^2=CH_2$, Z=CH, $R^1=CH_3$, $R^2=H$, Ar=4-Ph-Ph
48. 2,6-cis, $X^1=X^2=Y^1=Y^2=CH_2$, Z=CH, $R^1=H$, $R^2=H$, Ar=4-OH-Ph
49. 2,6-cis, $X^1=X^2=Y^1=Y^2=CH_2$, Z=CH, $R^1=H$, $R^2=H$, Ar=4-AcO-Ph
50. 2,6-cis, $X^1=X^2=Y^1=Y^2=CH_2$, Z=CH, $R^1=H$, $R^2=H$, Ar=2, 4-dichloro-Ph
51. 2,6-cis, $X^1=X^2=Y^1=Y^2=CH_2$, Z=CH, $R^1=CH_3$, $R^2=H$, Ar=2,4-dichloro-Ph
52. 2,6-cis, $X^1=X^2=Y^1=Y^2=CH_2$, Z=CH, $R^1=H$, $R^2=H$, Ar=1-Naphthyl
53. 2,6-cis, $X^1=X^2=Y^1=Y^2=CH_2$, Z=CH, $R^1=CH_3$, $R^2=H$, Ar=1-Naphthyl
54. 2,6-cis, $X^1=X^2=Y^1=Y^2=CH_2$, Z=CH, $R^1=H$, $R^2=H$, Ar=2-Naphthyl
55. 2,6-cis, $X^1=X^2=Y^1=Y^2=CH_2$, Z=CH, $R^1=CH_3$, $R^2=H$, Ar=2-Naphthyl
56. 2,6-cis, $X^1=X^2=Y^1=Y^2=CH_2$, Z=CH, $R^1=H$, $R^2=H$, Ar=Ph
57. 2,6-cis, $X^1=X^2=Y^1=Y^2=CH_2$, Z=CH, $R^1=CH_3$, $R^2=CH_3$, Ar=Ph
55. 2,6-cis, $X^1$, $Y^1=C\equiv C$, $X^2=Y^2=CH_2$, Z=C, $R^2=O$, $R^1=H$, Ar=Ph
59. 2,6-trans, $X^1$, $Y^1=C\equiv C$, $X^2=Y^2=CH_2$, Z=C, $R^2=O$, $R^1=H$, Ar=Ph Table 1 below summarizes the interaction of compounds listed in (III) with nicotinic receptors, SERT and VMAT2.

TABLE 1

| Compd. | [$^3$H]Nicotine Binding (Ki) α4β2* (μm) | [$^3$H]MLA Binding (Ki) α7* (μm) | Inhibition of Nicotine-Evoked $^{86}$Rb$^+$ Efflux$^a$ (IC$_{50}$) α4β2* (μm) | Inhibition of Nicotine-Evoked[$^3$H] DA Overflow$^b$ (IC$_{50}$) α6β2* (μm) | [$^3$H]DA Uptake (Ki) (μm) | Inhibition of Nicotine-Evoked[$^3$H] NE Overflow$^b$ (IC$_{50}$) α3β4* (μm) | [$^3$H]5-HT Uptake (Ki) SERT (μm) | Inhibition of [$^3$H]DTBZ binding (Ki) VMAT2 (μm) |
|---|---|---|---|---|---|---|---|---|
| 1 | 0.016 | 11.6 | 0.73 | 0.3 | 29.4 | 0.01 | 25.7 | 2.69 |
| 2 | 0.011 | 10.8 | 0.002 | 1.0 | 29.1 | ND | 1.67 | ND |
| 3 | 37.1 | 22.7 | ND | NI | 15.8 | ND | 3.31 | 3.07 |
| 4 | 3.1 | 3.29 | ND | NI | 33.3 | ND | 25.6 | 13.0 |
| 5 | 0.44 | 34.2 | 0.30 | NI | 1.74 | ND | 1.86 | 2.12 |
| 6 | 7.6 | 1.60 | ND | NI | 0.86 | ND | 0.04 | 5.06 |
| 7 | >100 | >100 | ND | NI | ND | ND | ND | 5.94 |
| 8 | 9.8 | >100 | ND | NI | ND | ND | ND | 3.55 |
| 9 | ND | ND | ND | ND | ND | ND | ND | ND |
| 10 | >100 | 1.25 | ND | ND | 6.62$^c$ | ND | 0.01$^c$ | 1.87 |
| 11 | 32 | >100 | ND | ND | ND | ND | ND | 2.80 |
| 12 | 1.21 | 36.4 | ND | ND | ND | ND | ND | 2.37 |
| 13 | ND | ND | ND | ND | ND | ND | ND | ND |
| 14 | >100 | >100 | NI | 0.0003 | 0.58 | 0.01 | 8.94 | 2.31 |
| 15 | 11.9 | >100 | ND | 1.0 | 0.26 | 0.03 | 0.38 | 18.5 |
| 16 | 12.3 | >100 | ND | ND | ND | ND | ND | ND |
| 17 | 77 | 43.1 | NI | NI | 1.95 | ND | 1.59 | 0.68 |
| 18 | >100 | 24.3 | ND | 0.003 | 3.69 | ND | 2.92 | 5.34 |
| 19 | >100 | ND | ND | ND | ND | ND | ND | 6.05 |
| 20 | >100 | >100 | ND | ND | ND | ND | ND | 2.04 |
| 21 | >100 | >100 | ND | ND | ND | ND | ND | 2.50 |
| 22 | >100 | 55.1 | ND | ND | ND | ND | ND | ND |
| 23 | >100 | >100 | ND | ND | ND | ND | ND | 2.07 |
| 24 | ND | ND | ND | ND | ND | ND | ND | ND |
| 25 | >100 | >100 | ND | 0.1 | 1.03 | ND | 2.51 | 2.29 |
| 26 | >100 | >100 | ND | ND | ND | ND | ND | 3.23 |
| 27 | >100 | >100 | ND | ND | ND | ND | ND | 1.80 |
| 28 | >100 | >100 | ND | ND | ND | ND | ND | 2.40 |
| 29 | ND | ND | ND | ND | ND | ND | ND | ND |
| 30 | >100 | >100 | ND | ND | ND | ND | ND | 1.60 |
| 31 | >100 | >100 | ND | ND | ND | ND | ND | 1.08 |
| 32 | ND | >100 | ND | ND | ND | ND | ND | 1.60 |
| 33 | >100 | >100 | ND | ND | ND | ND | ND | 0.56 |
| 34 | >100 | >100 | ND | ND | ND | ND | ND | 1.34 |
| 35 | >100 | >100 | ND | ND | ND | ND | ND | 0.61 |
| 36 | >100 | >100 | ND | ND | ND | ND | ND | 1.85 |
| 37 | >100 | 26.0 | ND | ND | ND | ND | ND | 0.58 |
| 38 | >100 | >100 | ND | ND | ND | ND | ND | 1.74 |
| 39 | >100 | 25.5 | ND | ND | ND | ND | ND | 0.43 |
| 40 | >100 | >100 | ND | ND | ND | ND | ND | ND |
| 41 | >100 | >100 | ND | ND | ND | ND | ND | 1.30 |
| 42 | >100 | >100 | ND | ND | ND | ND | ND | 3.23 |
| 43 | ND | >100 | ND | ND | ND | ND | ND | 4.42 |
| 44 | >100 | >100 | ND | ND | ND | ND | ND | ND |
| 45 | >100 | >100 | ND | ND | ND | ND | ND | 1.50 |
| 46 | ND | ND | ND | ND | ND | ND | ND | ND |

TABLE 1-continued

| Compd. | [³H]Nicotine Binding (Ki) α4β2* (μm) | [³H]MLA Binding (Ki) α7* (μm) | Inhibition of Nicotine-Evoked ⁸⁶Rb⁺ Efflux[a] (IC₅₀) α4β2* (μm) | Inhibition of Nicotine-Evoked[³H] DA Overflow[b] (IC₅₀) α6β2* (μm) | [³H]DA Uptake (Ki) (μm) | Inhibition of Nicotine-Evoked[³H] NE Overflow[b] (IC₅₀) α3β4* (μm) | [³H]5-HT Uptake (Ki) SERT (μm) | Inhibition of [³H]DTBZ binding (Ki) VMAT2 (μm) |
|---|---|---|---|---|---|---|---|---|
| 47 | ND | ND | ND | ND | ND | ND | ND | ND |
| 48 | >100 | >100 | ND | ND | ND | ND | ND | 5.20 |
| 49 | >100 | >100 | ND | ND | ND | ND | ND | 5.10 |
| 50 | >100 | >100 | ND | ND | ND | ND | ND | ND |
| 51 | >100 | >100 | ND | ND | ND | ND | ND | 1.07 |
| 52 | >100 | >100 | ND | ND | ND | ND | ND | ND |
| 53 | >100 | >100 | ND | ND | ND | ND | ND | ND |
| 54 | ND | ND | ND | ND | ND | ND | ND | ND |
| 55 | ND | ND | ND | ND | ND | ND | ND | ND |
| 56 | ND | ND | ND | ND | ND | ND | ND | ND |
| 57 | ND | ND | ND | ND | ND | ND | ND | ND |
| 58 | ND | ND | ND | ND | ND | ND | ND | ND |
| 59 | ND | ND | ND | ND | ND | ND | ND | ND |

ND: not determined
NI: no inhibition
[a]Inhibition of 1 μM S(−)-nicotine
[b]Inhibition of 10 μM S(−)-nicotine
[c]Data of a mixture of compound 10 and 11

The invention will now be discussed by certain examples that illustrate but do not limit the invention. Table 2 below summarizes the inhibition of methamphetamine-evoked endogenous DA release from striatal slices.

TABLE 2

| Compd. | Inhibition of Methamphetamine Evoked DA Overflow IC₅₀ (μM) (Mean) |
|---|---|
| 1 | 1.25 |
| 14 | 0.70 |
| 15 | >100 |
| 16 | 0.43 |
| 17 | 0.44 |
| 18 | >100 |
| 19 | >100 |

The 2,6-disubstituted piperidino and 2,6-disubstituted piperazino analogs listed in Table 1 have the chemical structure of formula (III). They were assayed for nicotinic receptor interaction (α4β2* and α6β2* and α3β4*; however, the * indicates the putative nature of the nicotinic receptors and does not limit the invention to other putative nicotinic receptor subtypes of native composition) and inhibition of dopamine transporter protein (DAT), the serotonin transporter (SERT), the norepinephrine transporter (NET), and the vesicular monoamine transporter (VMAT2) activity.

Selected compounds in Table 1 were evaluated in the high affinity [³H]nicotine binding assay and afforded inhibition constants (Ki values) ranging from 0.011 μM to greater than 100 μM. Three of these compounds were in the range of 11-440 nM. Ten compounds were in the range of 0.5-77 μM. Many compounds had Ki values greater than 100 μM.

Selected compounds in Table 1 were evaluated in the ⁸⁶Rb⁺ efflux assay using rat thalamic synapotosomes. This functional assay assesses the interaction of the compounds with the nicotinic receptor subtype probed by the [³H]nicotine binding assay and provides an initial indication if the compound acts as an agonist, partial agonist or antagonist at this receptor subtype. The compounds with the highest affinity in the [³H]nicotine binding assay were evaluated in the functional ⁸⁶Rb⁺ efflux assay and were shown to be potent inhibitors of nicotine-evoked ⁸⁶Rb⁺ efflux. IC₅₀ values were in the range 0.002 EM-0.73 tM. Thus, these compounds appear to act as nicotinic receptor antagonists.

Compounds in Table 1 were evaluated for their ability to inhibit [³H]methyllycaconitine ([³H]MLA) binding to rat whole brain membranes to assess potential interaction with the α7* nicotinic receptor sites. Some of the compounds show low affinity with a range of Ki values of 1.25 μM-55 μM. Many of the compounds exhibited Ki values greater than 100 μM at this nicotinic receptor subtype.

Compounds in Table 1 were evaluated for their ability to evoke or inhibit nicotine-induced [³H]dopamine ([³H]DA) or nicotine-induced [³H]norepinephrine ([³H]NE) release from superfused rat striatal and hippocampal slices in vitro to assess interaction with α6β2* and α3β4* nicotinic receptors, respectively (again, the * indicates the putative designation for the subunit composition of these nicotinic receptor subtypes and does not limit the invention to other subunit compositions for the nicotinic receptors). Two compounds (compounds 14 and 18) exhibited very potent inhibition if nicotine-evoked [³H]DA overflow (IC₅₀=0.3 and 3.0 nM). Four compounds (compounds 1, 2, 15 and 25) exhibited inhibition with IC 50 values in the range 0.1-1.0 μM. Several compounds showed no inhibition of the α6β2* nicotinic receptor (nicotinic receptor mediating nicotine-evoked [³H] DA release from striatum). With respect to compounds inhibiting nicotine-evoked [³H]NE overflow from hippocampus, several compounds exhibited IC50 values from 0.01-0.03 μM, showing inhibition at α3β4* nicotinic receptors.

The 2,6-disubstituted piperidino and 2,6-disubstituted piperazino analogs listed in Table 1 were also assayed for inhibition of DAT activity, i.e., inhibition of [³H]DA uptake into the dopaminergic presynaptic terminal. Eleven compounds were evaluated and afforded inhibition constants (Ki values) ranging from 0.26 μM to 33 μM. Removal of both functionalities of the lobeline molecule resulted in loss of affinity for the nicotinic receptor probed by [$^3$H]nicotine binding and a 15-100-fold more potent inhibition of the dopamine transporter (DAT) compared with lobeline. Removal of either the hydroxyl group or the keto group of lobeline resulted in a 50-fold loss of affinity for the nicotinic receptor. Interestingly, the ketoalkene analog inhibited DAT 17-fold more potently than lobeline, whereas lobelanidine inhibited DAT equipotently compared to lobeline. Conversion of the hydroxy group of lobeline to a bulky tosyloxy group did not alter the affinity at nicotinic receptors probed by [$^3$H]nicotine binding, and did not alter the interaction with the DA transporter. Trans-meso-transdiene (Compound 15) was the most potent compound in the DA uptake assay, but had 1000-fold lower affinity for the nicotinic receptor compared to lobeline. This data indicates that appropriate structural modification of the lobeline molecule affords compounds in which the interaction with DAT is enhanced. Furthermore, in one compound, i.e., meso-transdiene (Compound 14), the nicotinic receptor interaction has been eliminated and the compound is relatively selective for inhibition of DAT.

The 2,6-disubstituted piperidino and 2,6-disubstituted piperazino analogs of the present invention exhibited activity at the serotonin transporter (SERT). Three compounds (compounds 6, 10 and 15) exhibited inhibition of serotonin uptake with Ki values ranging from 0.01 μM-0.38 μM. A number of compounds exhibited Ki values in the range of 1.6 μM -26 μM.

The 2,6-disubstituted piperidino and 2,6-disubstituted piperazino analogs of the present invention exhibited activity at the vesicular monoamine transporter (VMAT2). Five compounds (compounds 17, 33, 35, 37, 39) exhibited inhibition of [$^3$H]DTBZ binding with Ki values in the range 0.43 μM-0.68 μM. A number of compounds exhibited Ki values in the range of 1.1 μM-18.5 μM.

The 2,6-disubstituted piperidino analogs of the present invention inhibited methamphetamine-evoked endogenous DA overflow from superfused rat striatal slices. Four compounds (compounds 1, 14, 16, and 17) exhibited IC50 values in the range 0.43 μM-1.25 μM. Compounds 15, 18 and 19 exhibited IC50 values greater than 100 μM.

Tables 3 below summarizes data from an earlier study of 2,6-disubstituted piperidino analogs of the present invention showing that they exhibit selectivity for either nAChRs and/or DAT. The previous data also shows that the analogs active towards the nicotinic receptor generally do not interact with the DAT, and those that interact with the DAT show only modest nicotinic receptor activity. The nine 2,6-disubstituted piperidino analogs listed in Table 3 have the chemical structure of formula (IV).

TABLE 3

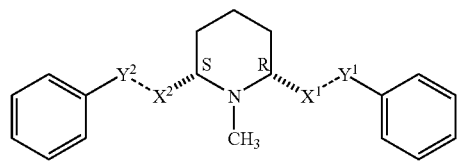

(IV)

| Compound | Ki (μM) [$^3$H]-Nicotine Binding Assay | Ki (μM) [$^3$H]-Dopamine Uptake Assay |
|---|---|---|
| 1. $X^1 = X^2 = CH_2$<br>$Y^1 = C=O$<br>$Y^2 = (S)—CHOH$ | 0.0043 | 45 |
| 17. $X^1 = X^2 = Y^1 = Y^2 = CH_2$ | 14.3 | 3.0 |
| 2. $X^1 = X^2 = CH_2$<br>$Y^1 = C=O$<br>$Y^2 = (S)—CHOSO_2—C_6H_4$-p-$CH_3$ | 0.0041 | 39 |
| 3. $X^1 = X^2 = CH_2$<br>$Y^1 = Y^2 = C=O$ | 11 | 25 |
| 14. $X^1,Y^1 = X^2,Y^2 = $ trans CH=CH | >100 | 0.8 |
| 5. $X^1 = CH_2$<br>$Y^1 = C=O$<br>$X^2,Y^2 = $ trans CH=CH | 0.13 | 3.0 |
| 4. $X^1 = X^2 = CH_2$<br>$Y^1 = (S)—CHOH$<br>$Y^2 = (R)—CHOH$ | 0.93 | 54 |
| 60. $X^1 = X^2 = Y^2 = CH_2$<br>$Y^1 = (RS)—CHOH$ | 0.16 | 8.9 |
| 7. $X^1 = CH_2$<br>$Y^1 = (S)—CHOH$<br>$X^2,Y^2 = $ trans CH=CH | 4.2 | 1.3 |

Compound 60 is a mixture of epimers from the earlier study. The mixture was subsequently separated providing the individual epimers, compounds 10 and 11 in Table 1.

The nine compounds in Table 3 were evaluated in the high affinity [$^3$H]nicotine binding assay and afforded inhibition constants (Ki values) ranging from 0.0043 μM to >100 μM. Five of these compounds had Ki values in the range of 4-160 nM. Three of these compounds had Ki values in the range of 0.93-14 μM. The cis-2,6-disubstituted piperidino analogs listed in Table 3 were also assayed for inhibition of DAT activity, i.e., inhibition of [$^3$H]DA uptake into the dopaminergic presynaptic terminal. Nine compounds in Table 3 were evaluated and afforded inhibition constants (Ki values) ranging from 0.08 μM to 54 μM.

Removal of both functionalities of the lobeline molecule resulted in loss of affinity for the nicotinic receptor and a 100-fold more potent inhibition of the dopamine transporter (DAT) compared with lobeline. Removal of either the hydroxyl group or the keto group of lobeline resulted in a 50-fold loss of affinity for the nicotinic receptor. Interestingly, the ketoalkene analog inhibited DAT 10-fold more potently than lobeline, whereas lobelanidine inhibited DAT equipotently compared to lobeline. Conversion of the hydroxy group of lobeline to a bulky tosyloxy group reduced the affinity of the nicotinic receptor by only 3-fold, but did not alter the interaction with the DA transporter. The hydroxyalkene had a similar potency with the meso-transdiene (the most potent compound) in the DA uptake assay, but had 1000-fold lower affinity for the nicotinic receptor. Also, the completely defunctionalized lobeline molecule and the hydroxyalkane analog were both less potent than the meso-transdiene in inhibiting DA uptake into striatal synaptosomes. This data indicates that appropriate structural modification of the lobeline molecule affords compounds in which the interaction with DAT is enhanced. Furthermore, in one compound, i.e., the meso-transdiene, the nicotinic receptor interaction has been eliminated and the compound is thus selective for inhibition of DAT.

Earlier studies of the 2,6-disubstituted piperidino analog Compounds 14 and 15 show that the compounds exhibit activity at either nAChRs and/or the serotonin transporter protein (SERT) and/or the vesicular monoamine transporter (VMAT2).

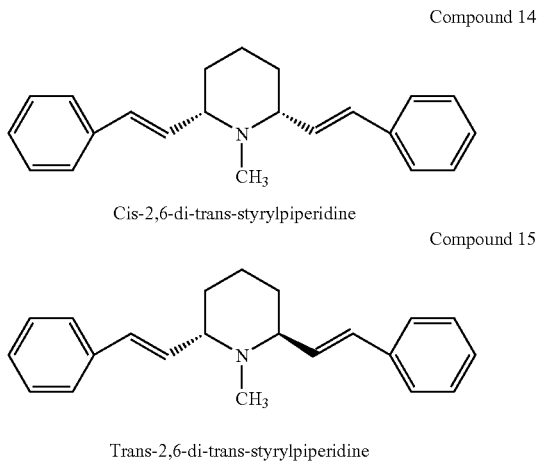

Compound 14

Cis-2,6-di-trans-styrylpiperidine

Compound 15

Trans-2,6-di-trans-styrylpiperidine

Table 4 below summarizes the data from the earlier studies showing interaction of Compound 14 and Compound 15 with nicotinic receptors, SERT and VMAT2.

vesicle membranes and inhibition of SERT function. Compound 15 exhibits good selectivity (9.5-fold) for the α6β2* subtype of nAChR relative to its interaction with the MTBZ site on VMAT2, as indicated by its ability to inhibit nicotine-evoked [$^3$H]DA release. Moreover, Compound 15 exhibits very good selectivity (>24-fold) for the α6β2* subtype of nAChR compared to its interaction with either α4β2* or α7* subtypes of nAChR. Furthermore, Compound 15 was only 2.2-fold more selective as an inhibitor of the α6β2* subtypes of nAChR compared to its inhibition of SERT function. Finally, Compound 15 interacted with SERT 4.3-fold more selectively than it interacted with VMAT2.

The earlier data shows that Compound 14 was 18-fold more potent at inhibiting nicotine-evoked [$^3$H]DA and [$^3$H]NE release from rat striatal and hippocampal slices, indicated a higher affinity for the α6β2* and α3β4* subtypes of nAChRs, compared to Compound 15. On the other hand, Compound 15 was 19-fold more potent inhibiting the function of SERT than was Compound 14. Finally, Compound 14 was only 4-fold more potent interacting with VMAT2 compared to Compound 15. Thus, alteration of stereochemistry at C2 and C6 from cis to trans resulted in a diminished affinity for the α6β2* subtypes of nAChR and for VMAT2, and enhanced the affinity for SERT, whereas there was no change in affinity for either α4β2* or α7* subtypes of nAChR. Therefore, cis-analogs have higher affinity for VMAT2 and α6β2* subtype of nAChRs.studies.

The 2,6-disubstituted piperidino and 2,6-disubstituted piperazino analogs of the present invention exhibit selectivity for either neuronal nicotinic acetylcholine receptors

TABLE 4

| Compound | [$^3$H]Nicotine Binding (Ki) α4β2* | [$^3$H]MLA Binding (Ki) α7* | Inhibition of Nicotine-Evoked $^{86}$Rb$^+$ Efflux$^a$ (IC$_{50}$) α4β2* | Inhibition of Nicotine-Evoked[$^3$H]DA Overflow$^b$ (IC$_{50}$) α6β2* | Inhibition of Nicotine-Evoked[$^3$H]NE Overflow$^b$ (IC$_{50}$) α3β4* | Inhibition of [$^3$H]MTBZ binding (IC$_{50}$) VMAT2 | [$^3$H]5-HT Uptake (IC$_{50}$) SERT |
|---|---|---|---|---|---|---|---|
| 14 | 11 μM | >100 μM | >10 μM | 0.03 μM | 0.021 | 1.29 μM | 23.2 μM |
| 15 | 13 μM | >100 μM | ND | 0.54 μM | ND | 5.15 μM | 1.19 μM |

$^a$Inhibition of 1 μM S(−)-nicotine
$^b$Inhibition of 10 μM S(−)-nicotine

The two 2,6-disubstituted piperidino analogs in Table 4 have the chemical structure of Formula II, and were assayed for interaction with α4β2*, α7*, α6β2* and α3β4* subtypes of nAChRs, interaction with VMAT2 located on vesicle membranes and inhibition of SERT function. It shall be noted that the nAChR subtypes for the activities described herein have not been elucidated conclusively, and thus, the asterisk is an indication of the putative nature of the receptor subtype mediating the action. Compound 14 exhibits good selectivity (43-fold) for the α6β2* subtype of nAChR relative to its interaction with the MTBZ site on VMAT2, as indicated by its ability to inhibit nicotine-evoked [$^3$H]DA release. Moreover, Compound 14 exhibits very good selectivity (>370-fold) for the α6β2* and α3β4* subtypes of nAChRs compared to its interaction with either α4β2* or α7* subtypes of nAChR. Furthermore, Compound 14 was 770-fold more selective as an inhibitor of the α6β2* and α3β4* subtypes of nAChR compared to its inhibition of SERT function. Finally, Compound 14 interacted with VMAT2 18-fold more potently than with SERT.

Compound 15 was also assayed for interaction with nAChRs subtypes, interaction with VMAT2 located on and/or the DAT, SERT, NET or VMAT2. The analogs that are active towards the nicotinic receptor generally do not interact with the DAT, and those that interact with the DAT show only modest nicotinic receptor activity.

The invention will now be discussed by certain examples that illustrate but do not limit the invention.

EXAMPLE 1

Cis-2,6-di-trans-styrylpiperidine 1.00 g (2.95 mmol) of lobelanidine was dissolved in 15 ml of 85% H$_3$PO$_4$ and allowed to stir overnight at 60° C. The reaction mixture was taken up in H$_2$O and made basic with solid K$_2$CO$_3$ (pH~8). The pH was adjusted by the addition of solid NaOH (pH~10). The aqueous solution was extracted three times with 15 ml of EtOAc. The organic layers were combined and dried over anhydrous MgSO$_4$. The salts were removed via filtration and solvent removed by rotary evaporation affording 0.70 g of crude product. This compound was recrystallized from MeOH affording 0.60 g of pure cis-2,6-di-trans-styrylpiperidine. Percent yield=78.6% Mp=139-

141° C. ¹H NMR (300 MHz, CDCl₃) d: 1.40-1.80 (m, 6H), 2.23 (s, 3H), 2.50-2.64 (t, 2H), 6.04-6.20 (dd, 2H), 6.39-6.50 (d, 2H) and 7.10-7.38 (m, 10H); ¹³C NMR (CDCl₃) d: 23,75, 33.56, 42.32, 68.36, 126.26, 127.38, 128.61, 130.52, 133.89 and 137.13 ppm.

EXAMPLE 2

Preparation of cis- and trans-2,6-di-trans-styrylpiperidine

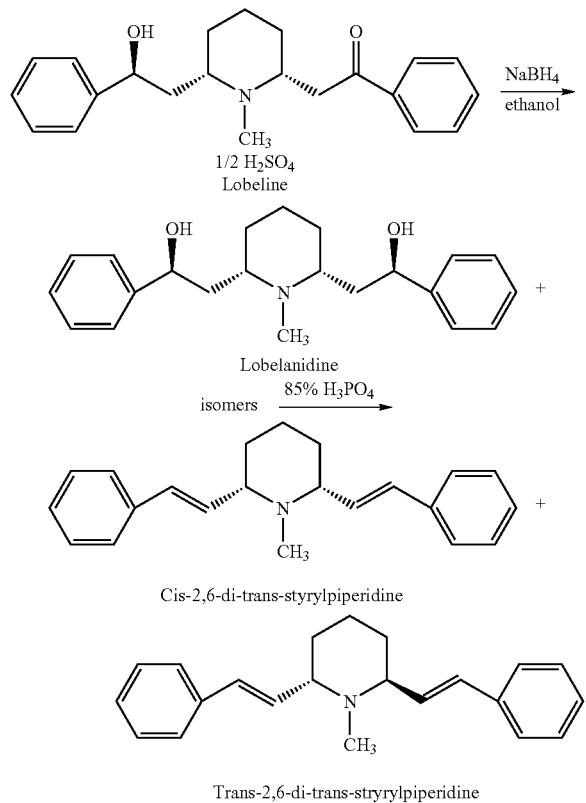

To a suspension of L-lobeline hemisulfate salt (85%, 10.5 g) in absolute ethanol (300 mL) was added NaBH₄ (1.5 eq.) portionwise at 0° C. The mixture was stirred at 0° C. for 1 hour, and then quenched with acetone. The mixture was evaporated under reduced pressure. Water (100 mL) was added to the residue and extracted with chloroform (80 mL×3). The combined organic extract was dried (MgSO₄), filtered and evaporated to afford lobelanidine as a white solid which was used directly. An analytical sample was recrystallized from acetone/hexane as a needle crystal. Mp 142-143° C.; ¹H NMR (300 MHz, CDCl₃) δ 1.15 (m, 2H), 1.44-1.82 (m, 6H), 2.04 (ddd, J=14.4, 10.2, 8.7 Hz, 2H), 2.35 (s, 3H), 2.96 (m, 2H), 4.89 (dd, J=8.7, 5.1 Hz, 2H), 7.23-7.50 (m, 10H); ¹³C NMR (75 MHz, CDCl₃) δ 23.48, 25.20, 25.96, 41.79, 62.37, 74.30, 125.98, 127.50, 128.55, 144.88 ppm.

Crude lobelanidine was dissolved in 130 mL 85% H₃PO₄ and allowed to stir at 60° C. for 24 hours. The reaction mixture was cooled to room temperature, diluted with 250 mL water and made basic with solid NaOH (pH~10). The aqueous solution was extracted with EtOAc (150 mL×3). The combined organic extract was dried (MgSO₄), filtered and concentrated under reduced pressure. The crude product was recrystallized from acetone affording 2.2 g of pure cis-2,6-di-trans-styrylpiperidine as a white solid. Mp: 105-106° C.(HCl salt); ¹H NMR (300 MHz, CDCl₃) δ 1.42-1.88 (m, 6H), 2.25 (s, 3H), 2.63 (m, 2H), 6.21 (dd, J=15.9, 9.0, 2H), 6.51 (d, J=15.9, 2H), 7.19-7.41 (m, 10H); ¹³C NMR (75 MHz, CDCl₃) δ 24.14, 33.94, 42.61, 68.56, 126.32, 127.46, 128.69, 130.51, 134.03, 137.17 ppm. The remaining mother liquor was evaporated and the residue was chromatographed (SiO₂, EtOAc/hexanes, 1/10) to afford cis-2,6-di-trans-styrylpiperidine 1.4 g and trans-2S, 6S-di-trans-styrylpiperidine 230 mg. Mp: 200-202° C. (HCl salt); ¹H NMR (300 MHz, CDCl₃) δ 1.60-1.75 (m, 4H), 1.82-1.97 (m, 2H), 2.27 (s, 3H), 3.38 (m, 2H), 6.38 (dd, J=15.9, 8.7, 2H), 6.52 (d, J=15.9, 2H), 7.17-7.42 (m, 10H); ¹³C NMR (75 MHz, CDCl₃) δ 19.57, 32.92, 41.96, 62.29, 126.39, 127.50, 128.69, 130.49, 131.78, 137.20 ppm.

EXAMPLE 3

Cis-10R,2S,6R- and Cis-10S,2S,6R—N-methyl-6-[1-(2-hydroxy-2-phenyl)-ethyl]-2-trans-styrylpiperidine In a 250 ml round bottom flask was added 0.80 g of cis-2S,6R—N-methyl-6-phenacyl-2-trans-styrylpiperidine, and 50 ml of ethanol. Sodium borohydride was added until all of the starting material was consumed (determined by TLC). The solution was cooled to 0° C. and acetone was added in small portions to quench the reaction. The solvents were evaporated to dryness and water was added precipitating 0.75 g of an off-white crystalline solid (1:1) mixture of diastereomers, which was purified on silica eluting with 75:25 (CHCl₃/EtOH). The yield of the product (a mixture of diastereomers) was 93.4%. ¹H NMR (300 MHz, CDCl₃) δ: 1.17-2.06 (m, 12H), 2.12 (s, 3H), 2.35 (s, 3H), 2.50-6.20 (m, 4H), 2.70-3.20 (m, 4H), 4.78-4.80 (dd, 1H), 5.04-5.14 (dd, 1H), 5.96-6.20 (m, 2H), 6.32-6.42 (dd, 2H) and 7.04-7.34 (m, 20H); ¹³C NMR (CDCl₃) δ: 23.69, 24.15, 26.74, 29.68, 33.26, 39.94, 41.10, 41.41, 62.93, 63.00, 65.62, 68.32, 71.76, 73.90, 125.46, 126.15, 126.19, 126.83, 127.01, 127.37, 128.16, 128.23, 128.50, 130.58, 132.61, 133.85, 136.83, 136.95, 145.32 and 145.45 ppm.

EXAMPLE 4

Cis-2S,6R—N-methyl-6-[1-(2-hydroxy-2-phenyl) ethyl]-2-phenylethylpiperidine 0.50 g (1.55 mmol) of cis-2S,6R—N-methyl-6-phenacyl-2-trans-styrylpiperidine was dissolved in 50 ml of ethanol and placed into a Parr hydrogenation apparatus with 0.10 g of 10% Pd-on-Carbon. After removal of air, hydrogen gas was introduced until a pressure of 40 psig was reached. The reaction was allowed to proceed for 48 hours. The Pd catalyst was removed through filtration with Celite, and ethanol was removed by rotary evaporation to afford 0.30 g of a yellow oil. The compound was purified by silica gel chromatography eluting with EtOAc to afford 0.25 g of the product. The yield was 50.0%. ¹H NMR (300 MHz, CDCl₃) δ: 0.70-0.90 (m, 6H), 1.18 (s, 3H), 1.40-1.90 (m, 6H), 2.44-2.56 (m, 2H), 4.56-4.60 (dd, 1H) and 7.04-7.30 (m, 10H); ¹³C NMR (CDCl₃) δ: 25.77, 29.24, 29.38, 29.42, 29.46, 29.68, 31.44, 35.93, 39.07, 74.64, 125.50, 125.85, 127.42, 128.17, 128.35, 128.37, 142.85 and 144.91 ppm.

EXAMPLE 5

Preparation of Compound 2: 2S,6R,8S-2-[6-(β-Para-toluenesulfonyloxyphenethyl)-1-methyl-2-piperidyl]-acetophenone

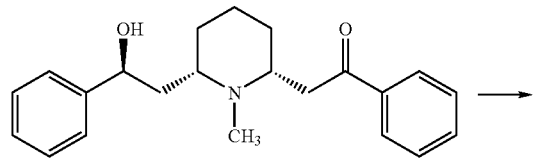

Compound 1

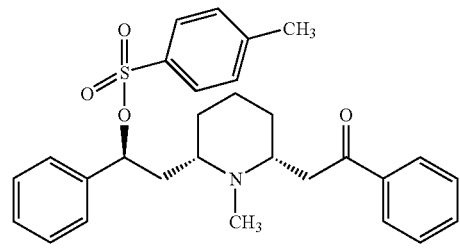

Compound 2

1.00 g (2.58 mmol) of lobeline hemisulfate was dissolved in 25 ml of pyridine and was added dropwise to a solution (cooled to 0° C.) containing 0.60 g (3.14 mmol) of p-toluenesulfonyl chloride dissolved in 15 ml of pyridine. After addition, the reaction was allowed to stir for 2 hours and then poured into 50 ml of ice-cold water and the mixture was stirred for an additional two hours. The aqueous solution was extracted three times with 25 ml of EtOAc. The organic layers were combined and dried over anhydrous $Na_2SO_4$. The salts were removed by filtration and the solvent was removed by rotary evaporation affording 450 mg of a pink-colored compound. The product was recrystallized from acetone yielding 300 mg of the product. Yield: 21.6%. mp=169-171° C.; $^1$H NMR (300 MHz, CDCl$_3$) δ 1.30-1.98 (m, 6H), 2.20 (s, 3H), 2.63-2.74 (d, 3H), 2.95-3.20 (m, 2H), 3.61-3.78 (d, 1H), 3.83-4.12 (m, 2H), 4.50-4.72 (m, 1H), 4.80-4.90 (d, 1H), 6.90-7.00 (d, 2H), 7.10-7.50 (m, 8H), 7.50-7.60 (d, 2H), 7.80-7.90 (d, 2H) and 9.85 (s, 1H) ppm; $^{13}$C NMR (75 MHz, CDCl$_3$) δ 21.16, 22.25, 23.32, 23.55, 27.35, 38.29, 40.18, 40.07, 60.79, 63.69, 71.05, 125.56, 125.76, 127.39, 128.28, 128.44, 128.69, 128.77, 133.67, 133.96, 135.87, 140.03, 141.98, 144.47, 195.21 ppm.

EXAMPLE 6

Preparation of Compound 5: N-methyl-2R-phenacyl-6S-trans-styrylpiperidine

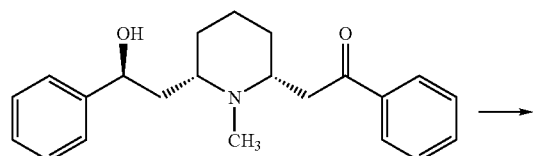

Compound 1

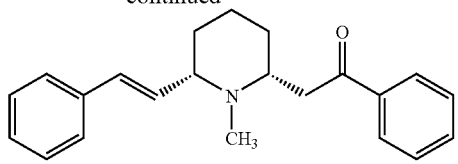

Compound 5

1.00 g (2.58 mmol) of lobeline hemisulfate was dissolved in 15 ml of 85% $H_3PO_4$ and the solution was allowed to stir for 24 hours at 50° C. Phosphoric acid was then neutralized with $K_2CO_3$, and a little ice cold $H_2O$ was added to dissolve the salts. The aqueous solution was extracted with ethyl acetate (20 mL×3). The organic layers were combined and dried with anhydrous MgSO$_4$. The salts were removed by filtration and the solvent was removed via rotary evaporation, affording 0.80 g of a gummy solid. Yield: 84.6%. $^1$H NMR (300 MHz, CDCl$_3$) δ 1.15-1.60 (m, 6H), 2.02 (s, 3H), 2.47-2.71 (m, 3H), 3.16-3.34 (dd, 1H), 5.80-6.00 (dd, 1H), 6.18-6.28 (d, 1H), and 6.90-7.38 (m, 8H) and 7.64-7.80 (d, 2H) ppm; $^{13}$C NMR (CDCl$_3$) δ 23.52, 32.56, 33.17, 40.52, 44.02, 59.62, 68.08, 126.00, 127.15, 127.92, 128.36, 128.44, 130.29, 132.91, 133.91, 136.95, 136.99, 198.83 ppm.

EXAMPLE 7

Preparation of Compound 6 and 7: N-Methyl-2R-(2R-hydroxy-2-phenethyl)-6S-trans-styrylpiperidine and N-Methyl-2R-(2S-hydroxy-2-phenethyl)-6S-trans-styrylpiperidine

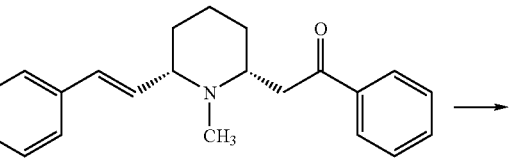

Compound 5

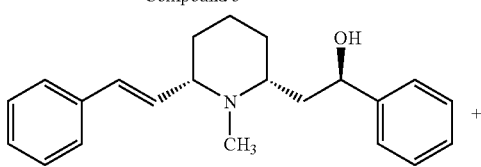

Compound 6

+

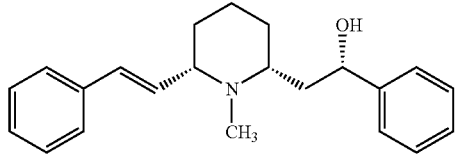

Compound 7

To a solution of compound 5 (1.25 g, 3.91 mmol) in absolute ethanol (40 mL) was added NaBH$_4$ (296 mg, 7.82 mmol) at 0° C. The mixture was stirred for 2 h at 0° C., and then quenched with acetone. The solvents were evaporated under reduced pressure, and the residue was suspended in water (80 mL) and extracted with CHCl$_3$ (3×50 mL). The combined organic extract was dried (Na$_2$SO$_4$), filtered and concentrated. Flash chromatography (CHCl$_3$/CH$_3$OH/NH$_4$OH 20:1:0.2) gave a 9:20 mixture of compound 6 and 7 as a white solid. Recrystallization from hexanes afforded 6 (308 mg, 24%) as a white solid. The remained mixture was purified by column chromatography (CHCl$_3$/CH$_3$OH/NH$_4$OH 50:1:0.2) to give 7 (511 mg, 41%) as a white solid. Compound 6: $[\alpha]_D^{25}$ 41.5 (c 1.0, CHCl$_3$); mp 104-105° C.; $^1$H NMR (300 MHz, CDCl$_3$) δ: 1.42-1.72 (m, 6H), 1.87 (m, 1H), 2.04 (m, 1H), 2.32 (s, 3H), 2.93 (m, 1H), 3.28 (m, 1H), 4.98 (dd, J=10.5, 3.3 Hz, 1H), 6.23 (dd, J=16.2, 6.3 Hz, 1H), 6.45 (d, J=16.2 Hz, 1H), 7.20-7.42 (m, 10H) ppm; $^{13}$C NMR (75 MHz, CDCl$_3$) δ 24.6, 26.7, 33.0, 41.5, 63.4, 65.5, 74.6, 125.6, 126.3, 127.2, 127.5, 128.4, 128.7, 130.4, 133.1, 137.2, 145.4 ppm; MS m/z 321 (M$^+$); Compound 7: mp 117-118° C.; $[\alpha]_D^{25}$-131.0 (c 1.0, CHC$_3$); $^1$H NMR (300 MHz, CDCl$_3$) δ 1.35-1.64 (m, 3H), 1.66-1.80 (m, 2H), 1.87 (m, 1H), 2.02 (m, 1H), 2.45 (m, 1H), 2.47 (s, 3H), 2.65 (m, 1H), 5.20 (dd, J=11.1, 3.3 Hz, 1H), 6.13 (dd, J=16.2, 8.4 Hz, 1H), 6.47 (d, J=16.2 Hz, 1H), 7.20-7.42 (m, 10H); 13C NMR (75 MHz, CDCl3) δ 24.0, 30.0, 33.7, 40.2, 41.6, 63.3, 68.6, 72.1, 125.6, 126.3, 127.0, 127.5, 128.3, 128.7, 130.7, 134.1, 137.0, 145.4 ppm; MS m/z 321 (M$^+$).

EXAMPLE 8

Preparation of Compound 10: N-Methyl-2R-(2R-hydroxy-2-phenethyl)-6S-(2-phenethyl) piperidine

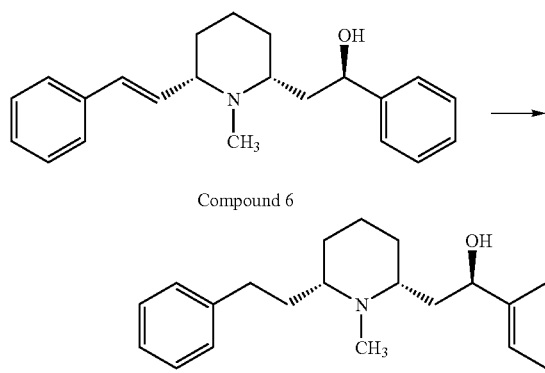

Compound 6

Compound 10

Compound 6 (230 mg, 0.72 mmol) was suspended in absolute methanol (30 mL) and 10% Pd/C (30 mg) was added. The mixture was hydrogenated on a Parr hydrogenation apparatus (45 psi) for 36 hours. The catalyst was removed by filtration through Celite. The filter cake was rinsed with methanol, and the combined organic portions were concentrated under reduced pressure. The resulting residue was purified by column chromatography (CHCl3/CH3OH/NH4OH 40:1:0.2) to afford 10 (187 mg, 81%) as colorless oil. $[\alpha]_D^{25}$ 65.5 (c 1.0, CHCl$_3$); $^1$H NMR (300 MHz, CDCl$_3$) δ 1.14 (m, 1H), 1.25 (m, 1H), 1.45-1.70 (m, 5H), 1.76-2.04 (m, 3H), 2.30 (s, 3H), 2.57-2.79 (m, 2H), 2.87 (m, 1H), 3.20 (m, 1H), 5.01 (dd, J=10.8, 3.0 Hz, 1H), 7.15-7.43 (m, 10H) ppm; $^{13}$C NMR (75 MHz, CDCl$_3$) δ 23.7, 23.9, 25.4, 25.7, 32.6, 36.0, 40.2, 62.0, 65.0, 76.4, 125.6, 125.9, 127.1, 128.4, 128.5, 128.6, 142.3, 145.2 ppm; MS m/z 323 (M$^+$);

EXAMPLE 9

Preparation of Compound 11: N-Methyl-2R-(2S-hydroxy-2-phenethyl)-6S-(2-phenethyl) piperidine

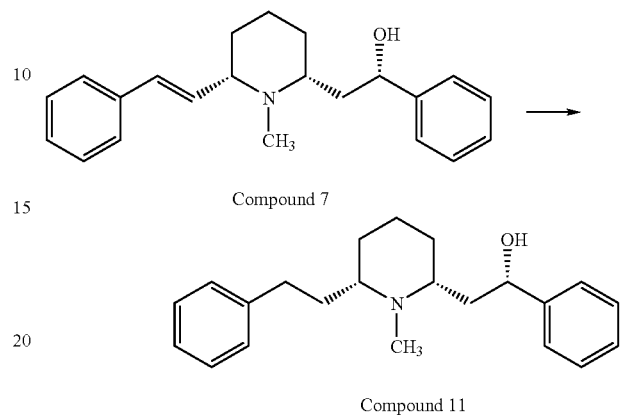

Compound 7

Compound 11

Compound 11 was prepared as described above for 10 from 7 (122 mg, 0.38 mmol) to give 92 mg (75%) of product as colorless oil. $[\alpha]_D^{25}$-75.4 (c 1.0, CHCl$_3$); $^1$H NMR (300 MHz, CDCl$_3$) δ 1.26-1.44 (m, 2H), 1.44-1.57 (m, 2H), 1.67-2.00 (m, 6H), 2.36 (m, 1H), 2.39 (s, 3H), 2.60-2.72 (m, 3H), 5.14 (t, J=6.0 Hz, 1H), 7.15-7.40 (m, 10H) ppm; $^{13}$C NMR (75 MHz, CDCl$_3$) δ 24.7, 26.7, 31.5, 33.7, 36.1, 39.1, 61.8, 62.8, 72.5, 125.7, 125.9, 126.8, 128.3, 128.5, 142.4, 145.7 ppm; MS m/z 323 (M$^+$);

EXAMPLE 10

Preparation of Compound 14 and 15: N-methyl-2,6-cis-di-trans-styrylpiperidine and N-methyl-2S,6S-trans-di-trans-styrylpiperidine

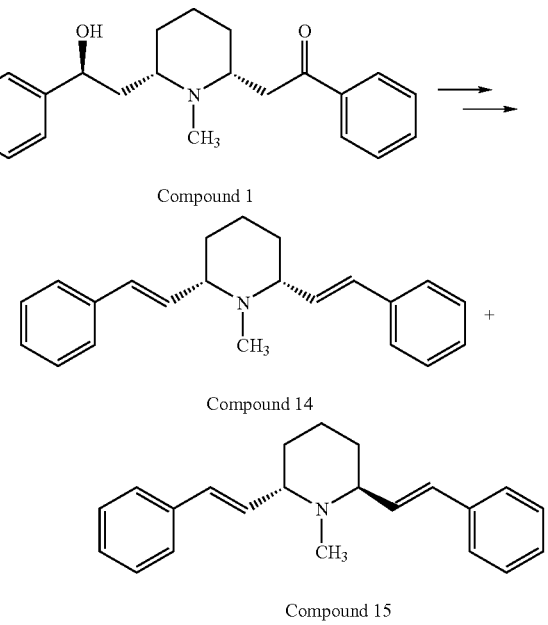

Compound 1

Compound 14

Compound 15

(−)-Lobeline semisulfate salt (1.85 g) was dissolved in saturated aqueous K₂CO₃ (60 mL) and extracted with CHCl₃ (3×30 mL). The combined organic phase was dried over anhydrous K₂CO₃ for 48 hours, filtered and concentrated to afford a mixture of 2R, 6S- and 2S, 6 S-lobeline free base in nearly equal ratio (determined by NMR) as a white solid (1.35 g, 4.00 mmol), which was suspended in absolute ethanol (40 mL) and NaBH₄ (300 mg, 8.00 mmol) was added at room temperature. The mixture was stirred for 1 hour, and then quenched with acetone. The solvents were evaporated under reduced pressure, and the residue was suspended in water (60 mL) and extracted with CHCl₃ (3×50 mL). The combined organic extract was dried (Na₂SO₄), filtered and concentrated to give a mixture of lobelanidine and its isomers as a white solid which was used directly. The crude product was dissolved in 85% H₃PO₄ (40 mL) and allowed to stir at 60° C. for 24 hours. The reaction mixture was cooled to room temperature, diluted with water (150 mL) and made basic with solid K₂CO₃ and then NaOH (pH~10). The aqueous solution was extracted with EtOAc (3×80 mL). The combined organic extract was dried (Na₂SO₄), filtered and concentrated. The crude product was purified by column chromatography (10:1 to 1:1 hexanes: ethylacetate gradient) to give title Compound 14 (390 mg, 32%) and 15 (341 mg, 28%) as white solids. Compound 14: mp 149-150° C.; ¹H NMR (300 MHz, CDCl₃) δ 1.42-1.88 (m, 6H), 2.25 (s, 3H), 2.63 (m, 2H), 6.21 (dd, J=15.9, 9.0 Hz, 2H), 6.51 (d, J=15.9 Hz, 2H), 7.19-7.41 (m, 10H) ppm; ¹³C NMR (75 MHz, CDCl₃) δ 24.1, 33.9, 42.6, 68.6, 126.3, 127.5, 128.7, 130.5, 134.0, 137.2 ppm; MS m/z 303 (M⁺). Compound 6b: [α]$_D^{25}$-180.2 (c 1.0, CHCl₃) mp 93-94° C.; ¹H NMR (300 MHz, CDCl₃) δ 1.60-1.75 (m, 4H), 1.82-1.97 (m, 2H), 2.27 (s, 3H), 3.38 (m, 2H), 6.38 (dd, J=15.9, 8.7 Hz, 2H), 6.52 (d, J=15.9 Hz, 2H), 7.17-7.42 (m, 10H) ppm; ¹³C NMR (75 MHz, CDCl₃) δ 19.6, 32.9, 42.0, 62.3, 126.4, 127.5, 128.7, 130.5, 131.8, 137.2 ppm; MS m/z 303.

EXAMPLE 11

Preparation of Compound 16:
N-methyl-2R,6R-trans-di-trans-styryl piperidine

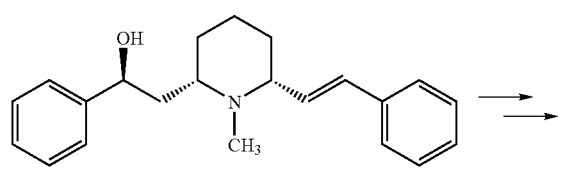

Compound 8

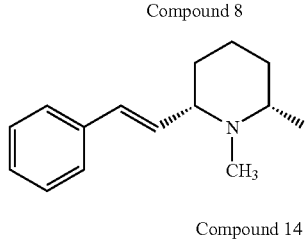

Compound 14

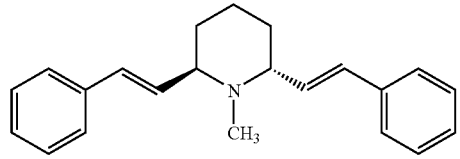

Compound 16

To a solution of Compound 8 (680 mg, 2.16 mmol) in CH₂Cl₂ (35 ml) was added celite (1 g) and PCC (912 mg, 4.23 mmol) at room temperature. The mixture was stirred for 6 h at rt, and then filtered through silica gel column, washed with 10% MeOH in CHCl₃. The product was kept at room temperature for 48 hours before removed the solvents, and then following the similar procedure for Compounds 14 and 15, Compound 16 was prepared to give 115 mg (18%) as a white solid along with Compound 14. Yield: 112 mg (17%). [α]$_D^{25}$ 182.8 (c 1.0, CHCl₃); mp 92-93° C.; ¹H NMR (300 MHz, CDCl₃) δ 1.62-1.75 (m, 4H), 1.80-1.96 (m, 2H), 2.28 (s, 3H), 3.38 (m, 2H), 6.38 (dd, J=15.9, 8.7 Hz, 2H), 6.52 (d, J=15.9 Hz, 2H), 7.20-7.42 (m, 10H) ppm; ¹³C NMR (75 MHz, CDCl₃) δ 19.6, 32.9, 41.9, 62.3, 126.4, 127.5, 128.7, 130.5, 131.7, 137.2 ppm; MS m/z 303.

EXAMPLE 12

Preparation of Compound 17: N-methyl-2,6-cis-di-(2-phenethyl)piperidine

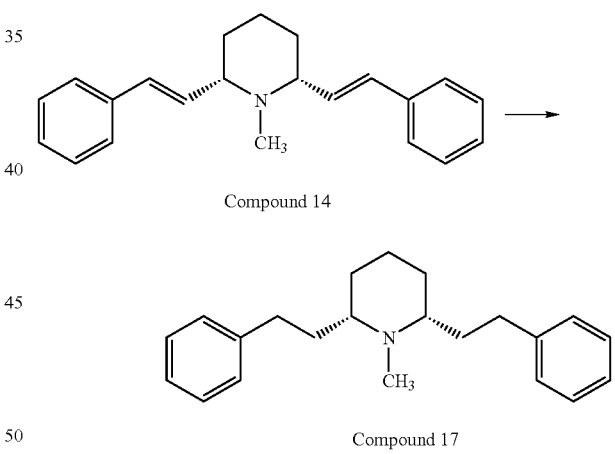

Compound 14 (420 mg, 1.38 mmol) was dissolved in methanol (50 mL) and 10% Pd/C (40 mg) was added. The mixture was hydrogenated on a Parr hydrogenation apparatus (45 psi) for 18 hours. The catalyst was removed by filtration through Celite. The filter cake was rinsed with methanol, and the combined organic portions were concentrated under reduced pressure. The resulting residue was purified by column chromatography to afford Compound 17. Yield: 223 mg (53%) as a white solid. mp 171-172° C.; ¹H NMR (300 MHz, CDCl₃) δ 1.30-1.42 (m, 4H), 1.60-1.85 (m, 6H), 2.19 (s, 3H), 2.32-2.44 (m, 2H), 2.60-2.77 (m, 4H), 7.12-7.35 (m, 10H) ppm; ¹³C NMR (75 MHz, CDCl₃) δ 25.4, 27.1, 31.0, 32.5, 36.6, 62.7, 125.7, 128.4, 128.5, 143.0 ppm; MS m/z 307 (M⁺).

EXAMPLE 13

Preparation of Compound 18: N-methyl-2S,6S-trans-di-(2-phenethyl)piperidine

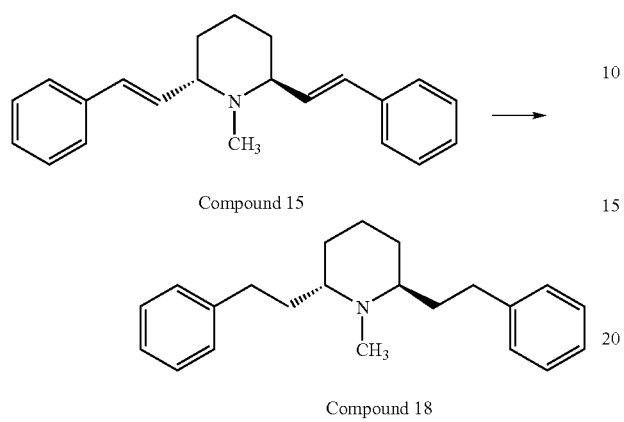

Compound 15

Compound 18

Compound 18 was prepared as described above for Compound 17 from Compound 15 (100 mg, 0.33 mmol) to give 52 mg (51%) of product as a colorless oil. $[\alpha]_D^{25}$ –35.4 (c 0.5, CHCl$_3$); $^1$H NMR (300 MHz, CDCl$_3$) δ 1.37-1.52 (m, 2H), 1.55-1.75 (m, 6H), 1.81-1.95 (m, 2H) 2.36 (s, 3H), 2.55-2.67 (m, 4H), 2.67-2.78 (m, 2H), 7.14-7.35 (m, 10H) ppm; $^{13}$C NMR (75 MHz, CDCl$_3$) δ 20.1, 26.6, 32.4, 33.1, 37.9, 57.6, 125.8, 128.4, 128.5, 142.9 ppm; MS m/z 307 (M$^+$).

EXAMPLE 14

Preparation of Compound 19: N-methyl-2R,6R-trans-di-(2-phenethyl)piperidine

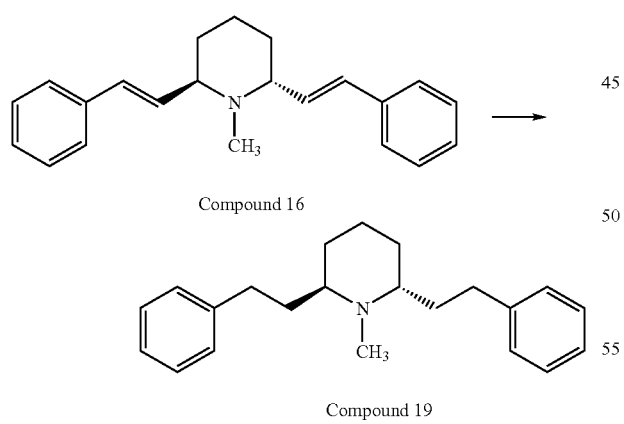

Compound 16

Compound 19

Compound 19 was prepared as described above for Compound 17 from Compound 16 (108 mg, 0.36 mmol) to give 53 mg (48%) of product as a colorless oil. $[\alpha]_D^{25}$ 36.0 (c 1.0, CHCl$_3$); $^1$H NMR (300 MHz, CDCl$_3$) δ 1.37-1.52 (m, 2H), 1.55-1.75 (m, 6H), 1.81-1.95 (m, 2H) 2.36 (s, 3H), 2.55-2.67 (m, 4H), 2.67-2.78 (m, 2H), 7.14-7.35 (m, 10H); $^{13}$C NMR (75 MHz, CDCl$_3$) δ 20.1, 26.6, 32.4, 33.1, 37.9, 57.6, 125.8, 128.4, 128.5, 142.9 ppm; MS m/z 307 (M$^+$).

EXAMPLE 15

Preparation of Compound 20: N-methyl-2R-(2-phenethyl)-6S-trans-styrylpiperidine

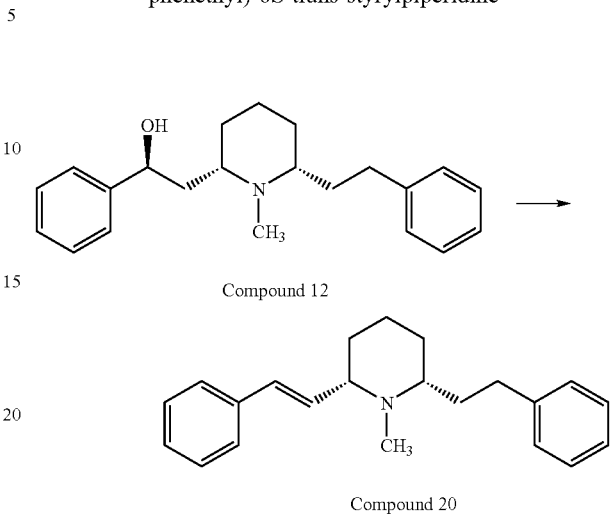

Compound 12

Compound 20

Compound 20 was prepared by dehydration method as described above for compound 14 and 15 from compound 12 (419 mg 1.30 mmol) to give 215 mg (54%) of product as white solid. $[\alpha]_D^{25}$ –51.5 (c 1.0, CHCl$_3$); mp 72-73° C.; $^1$H NMR (300 MHz, CDCl$_3$) δ 1.30-1.84 (m, 7H), 1.92-2.09 (m, 2H), 2.27 (s, 3H), 2.51-2.69 (m, 2H), 2.70-2.83 (m, 1H), 6.21 (dd, J=15.9, 8.4 Hz, 1H), 6.47 (d, J=15.9 Hz, 1H), 7.15-7.40 (m, 10H) ppm; $^{13}$C NMR (75 MHz, CDCl3) δ 24.5, 31.2, 31.9, 33.7, 36.2, 40.2, 63.9, 68.9, 125.8, 126.3, 127.4, 128.4, 128.5, 128.7, 130.2, 134.8, 137.3, 142.9 ppm; MS m/z 305 (M$^+$).

EXAMPLE 16

Preparation of compounds 21 and 22: N-methyl-2R-trans-styryl-6S-(2-phenethyl)piperidine and N-methyl-2S-trans-styryl-6S-(2-phenethyl)piperidine

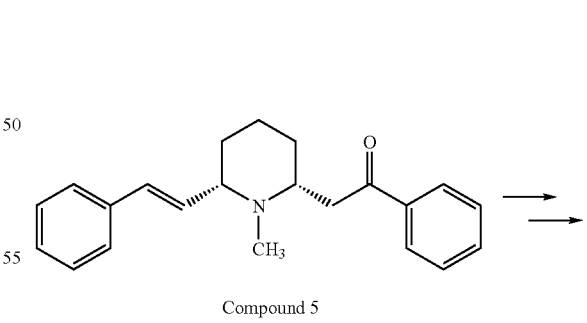

Compound 5

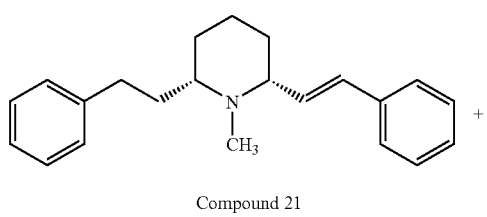

Compound 21

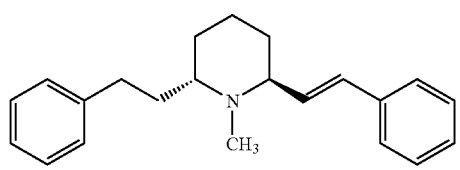

Compound 22

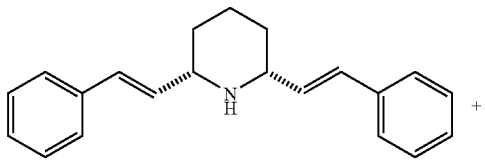

Compound 23

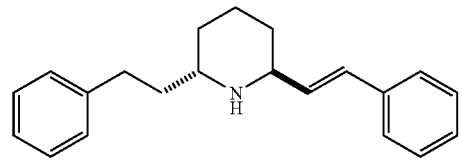

Compound 24

Compound 5 (1.20 g, 3.76 mmol) was dissolved in CHCl$_3$ (100 mL) and kept at room temperature for 48 hours. The solvent was removed under reduced pressure and the residue was dissolved in 10% HOAc/CH$_3$OH (100 mL) and 10% Pd/C (120 mg) was added. The mixture was hydrogenated on a Parr hydrogenation apparatus (45 psi) for 24 hours. The catalyst was removed by filtration through Celite. The filter cake was rinsed with methanol, and the combined organic portions were concentrated under reduced pressure. The crude product was dissolved in 85% H$_3$PO$_4$ (30 mL) and allowed to stir at 60° C. for 24 hours. The reaction mixture was cooled to room temperature, diluted with water (100 mL) and made basic with solid K$_2$CO$_3$ and then NaOH (pH~10). The aqueous solution was extracted with EtOAc (3×80 mL). The combined organic extract was dried (MgSO$_4$), filtered and concentrated. The crude product was purified by column chromatography (4:1 to 1:1 hexanes: ethylacetate gradient) to give Compound 21 (188 mg, 16%) as a white solid and Compound 22 (167 mg, 15%) as a colorless oil. Compound 21: $[\alpha]_D^{25}$ 53.8 (c 1.0, CHCl$_3$); mp 75-76° C.; $^1$H NMR (300 MHz, CDCl$_3$) δ 1.30-1.89 (m, 7H), 1.92-2.09 (m, 2H), 2.27 (s, 3H), 2.51-2.69 (m, 2H), 2.70-2.83 (m, 1H), 6.21 (dd, J=15.9, 8.4 Hz, 1H), 6.47 (d, J=15.9 Hz, 1H), 7.15-7.40 (m, 10H) ppm; $^{13}$C NMR (75 MHz, CDCl$_3$) δ 24.5, 31.3, 31.9, 33.7, 36.2, 40.3, 63.9, 68.9, 125.8, 126.3, 127.4, 128.4, 128.5, 128.7, 130.2, 134.9, 137.3, 142.9 ppm; MS m/z 305 (M$^+$). Compound 22: $[\alpha]_D^{25}$ −103.6 (c1.0, CHCl$_3$); $^1$H NMR (300 MHz, CDCl3) δ 1.50-1.82 (m, 7H), 1.84-1.98 (m, 1H), 2.32 (s, 3H), 2.51 (ddd, J=13.5, 10.8, 5.7 Hz, 1H), 2.68 (ddd, J=13.5, 10.8, 5.4 Hz, 1H), 2.83 (m, 1H), 3.23 (m, 1H), 6.28 (dd, J=15.9, 8.4 Hz, 1H), 6.47 (d, J=15.9 Hz, 1H), 7.13-7.39 (m, 10H) ppm; $^{13}$C NMR (75 MHz, CDCl3) δ 19.4, 28.9, 29.1, 32.2, 33.2, 40.7, 58.6, 61.8, 125.9, 126.4, 127.4, 128.4, 128.5, 128.7, 131.0, 132.0, 137.3, 142.7 ppm; MS m/z 305 (M$^+$).

EXAMPLE 17

Preparation of Compounds 23 and 24: 2,6-cis-di-trans-styrylpiperidine and (±)-2,6-trans-di-trans-styrylpiperidine

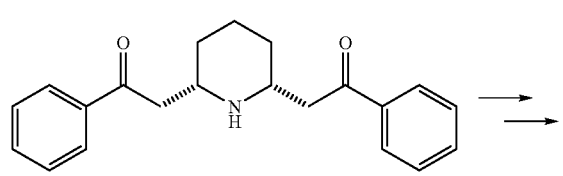

Cis-nor-lobelanine was prepared according to reported method (Ebnöther, 1958). With the similar procedure as Compounds 14 and 15 from (−)-lobeline 1, Compounds 23 and 24 were obtained in pure form. Compound 23: $^1$H NMR (300 MHz, CDCl$_3$) δ 0.78 (t, J=7.5 Hz, 3H), 1.28-1.60 (m, 3H), 1.68-1.84 (m, 2H), 1.91 (m, 1H), 3.37 (m, 2H), 6.26 (dd, J=15.9, 7.2 Hz, 2H), 6.54 (d, J=15.9 Hz, 2H), 7.17-7.40 (m, 10H) ppm; $^{13}$C NMR (75 MHz, CDCl$_3$) δ 24.7, 32.4, 59.7, 126.4, 127.4, 128.6, 129.6, 133.4, 137.2 ppm; MS m/z 289 (M$^+$), 198 (100), 156, 129, 115, 91. $^1$H NMR (300 MHz, CDCl$_3$) δ 0.78 (t, J=7.5 Hz, 3H), 1.53-1.90 (m, 6H), 3.78 (m, 2H), 6.41 (dd, J=15.9, 6.3 Hz, 2H), 6.52 (d, J=15.9 Hz, 2H), 7.19-7.43 (m, 10H) ppm; $^{13}$C NMR (75 MHz, CDCl$_3$) δ 20.3, 31.5, 53.8, 126.4, 127.5, 128.7, 129.9, 132.8, 137.3 ppm; MS m/z 289 (M$^+$), 198 (100), 156, 129, 115,91.

EXAMPLE 18

Preparation of Compounds 25-55

Compounds 25-55 were prepared as illustrated in the Scheme 1 below:

Scheme 1

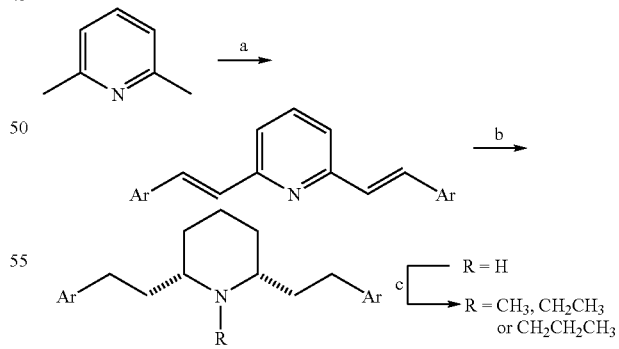

Reagents and conditions: (a) ArCHO, Ac$_2$O, reflux; (b) Pt$_2$O/H$_2$, HOAc; (c) R=CH$_3$, (CH$_2$O)$_n$, NaCNBH$_3$, MeOH; R=CH$_2$CH$_3$, EtI, K$_2$CO$_3$, THF, reflux, 72 h; R=CH$_2$CH$_2$CH$_3$, 1-PrI, K$_2$CO$_3$, THF, reflux, 72 h. The general procedure for preparing 2,6-di-arylenethenylpyridine, 2,6-cis-diarylethylpiperidine, N-methyl-2,6-cis-diarylethylpiperidine compounds is set forth below.

2,6-Di-arylenethenylpyridines: The mixture of 2,6-lutidine (5.32 g, 50 mmol), aryl aldehyde (105 mmol) and acetic anhydride (10 mL) was refluxed for 48-72 h and then cooled to room temperature. The solidified mixture was transferred to a suction filter and the filter cake was washed with 95% ethanol. If the reaction mixture could not be solidified, 95% ethanol was added and stirred until the product was precipitated. The crude product was recrystallized from benzene or ethanol to afford title compound as a white crystal. Yield: 20-93%.

2,6-Cis-Diarylethylpiperidines: The above 2,6-di-arylenethenylpyridine (10 mmol) was dissolved in glacial acetic acid (30 mL) and $PtO_2$ (1-2% w/w) was added. The mixture was hydrogenated on a Parr hydrogenation apparatus (45 psi) for 12-48 hours. The catalyst was removed by filtration through Celite. The filter cake was rinsed with methanol, and the combined organic portions were concentrated under reduced pressure. The resulting residue was basified with saturated aqueous $K_2CO_3$ and the aqueous solution was extracted with $CHCl_3$ (3×50 mL). The combined organic extract was dried ($Na_2SO_4$), filtered and concentrated. The crude product was purified by column chromatography (30:1 $CHCl_3$:MeOH) to give title compound. Yield: 53-90%.

N-methyl-2,6-cis-diarylethylpiperidines: $NaCNBH_3$ (188 mg, 3 mmol) was added to the mixture of nor-lobelane (1.00 mmol), paraformaldehyde (150 mg, 5.00 mmol) and methanol (10 mL). The mixture was stirred at room temperature for 2 hours. The solvent was then evaporated under reduced pressure. The residue was dissolved water (30 mL) and the aqueous solution was extracted with $CHCl_3$ (3×20 mL). The combined organic extract was dried ($Na_2SO_4$), filtered and concentrated. The crude product was purified by column chromatography (30:1 $CHCl_3$:MeOH) to give title compound. Yield: >95%.

Compound 25: 2,6-cis-diphenethylpiperidine $^1$H NMR (300 MHz, $CDCl_3$) δ 1.07 (ddd, J=24.0, 13.2, 3.9 Hz, 2H), 1.32 (ddt, J=26.4, 12.9, 3.9 Hz), 1.62-1.74 (m, 6H), 1.78 (dq, J=13.2, 3.0 Hz, 1H), 2.50 (m, 2H), 2.63 (t, J=8.1 Hz, 4H), 7.12-7.33 (m, 10H) ppm; $^{13}$C NMR (75 MHz, $CDCl_3$) δ 25.0, 32.7, 32.9, 39.2, 56.9, 125.9, 128.4, 128.5, 142.3 ppm; MS m/z 293 ($M^+$).

Compound 26: N-ethyl-2,6-cis-diphenethylpiperidine $^1$H NMR (300 MHz, $CDCl_3$) δ 0.94 (t, J=7.2 Hz, 3H), 1.28-1.48 (m, 3H), 1.56-1.82 (m, 5H), 1.86-2.02 (m, 2H), 2.46-2.80 (m, 8H), 7.13-7.31 (m, 10H) ppm; $^{13}$C NMR (75 MHz, $CDCl_3$) δ 12.6, 24.5, 28.8, 32.7, 36.0, 39.6, 60.7, 125.8, 128.4, 142.7 ppm; MS m/z 321 ($M^+$), 281, 216 (100), 188, 91.

Compound 27: N-(n-propyl)-2,6-cis-diphenethylpiperidine $^1$H NMR (300 MHz, $CDCl_3$) δ 0.78 (t, J=7.5 Hz, 3H), 1.28-1.47 (m, 5H), 1.52-1.89 (m, 7H), 2.41-2.78 (m, 8H), 7.14-7.33 (m, 10H) ppm; $^{13}$C NMR (75 MHz, $CDCl_3$) δ 12.1, 22.3, 24.6, 28.1, 33.1, 36.5, 48.3, 61.6, 125.8, 128.46, 128.51, 142.8 ppm; MS m/z 335 ($M^+$), 306, 230 (100), 202, 91.

Compound 28: 2,6-cis-di-(3,4-methylenedioxyphenethylpiperidine $^1$H NMR (300 MHz, $CDCl_3$) δ 1.06 (ddd, J=24.0, 12.9, 3.6 Hz, 2H), 1.31 (ddt, J=25.8, 12.9, 3.6 Hz, 1H), 1.52-1.73 (m, 6H), 1.78 (ddd, J=13.2, 6.3, 3.0 Hz, 1H), 2.47 (m, 2H), 2.55 (t, J=8.1 Hz, 4H), 5.90 (s, 4H), 6.62 (dd, J=7.8, 1.8 Hz, 2H), 6.67 (d, J=1.8 Hz, 2H), 6.72 (d, J=7.8 Hz, 2H) ppm; $^{13}$C NMR (75 MHz, $CDCl_3$) δ 25.0, 32.4, 32.9, 39.4, 56.7, 100.9, 108.3, 108.9, 121.1, 136.1, 145.6, 147.6 ppm; MS m/z 381 ($M^+$).

Compound 29: N-methyl-2,6-cis-di-(3,4-methylenedioxyphenethylpiperidine $^1$H NMR (300 MHz, $CDCl_3$) δ 1.25-1.49 (m, 4H), 1.60-1.89 (m, 6H), 2.21 (s, 3H), 2.34 (m, 2H), 2.56 (t, J=8.1 Hz, 4H), 5.94 (s, 4H), 6.64 (dd, J=7.8, 1.8 Hz,2H), 6.70 (d, J=1.8 Hz, 2H), 6.75 (d, J=7.8 Hz, 2H) ppm; $^{13}$C NMR (75 MHz, $CDCl_3$) δ 25.4, 29.1, 32.2, 32.7, 37.3, 62.9, 101.8, 108.5, 109.4, 121.6, 136.8, 144.9, 148.5 ppm;

Compound 30: 2,6-cis-di-(o-fluorophenethyl)piperidine $^1$H NMR (300 MHz, $CDCl_3$) δ 1.08 (ddd, J=24.0, 12.9, 3.9 Hz, 2H), 1.33 (ddt, J=25.8, 12.9, 3.9 Hz, 1H), 1.59-1.75 (m, 6H), 1.79 (ddd, J=12.9, 6.0, 3.0 Hz, 1H), 2.50 (m, 1H), 2.69 (t, J=7.8 Hz, 4H), 6.96-7.09 (m, 4H), 7.12-7.22 (m, 4H) ppm; $^{13}$C NMR (75 MHz, $CDCl_3$) δ 25.0, 25.7, 32.8, 37.9, 56.8, d(115.150, 115.454), d(124.050, 125.095), d(127.497, 127.603), d(129.031, 129.243), d(130.534, 130.595), d(159.525, 162.760) ppm; MS 329, 206, 109;

Compound 31: N-methyl-2,6-cis-di-(o-fluorophenethyl)piperidine $^1$H NMR (300 MHz, $CDCl_3$) δ 1.32-1.52 (m, 5H), 1.68 (m, 2H), 1.74-1.87 (m, 3H), 2.18 (s, 3H), 2.37 (m, 2H), 2.70 (m, 4H), 6.96-7.06 (m, 4H), 7.12-7.24 (m, 4H) ppm; $^{13}$C NMR (75 MHz, $CDCl_3$) δ 25.2, 25.7, 27.0, 30.9, 35.0, 62.7, d(115.214, 115.435), d(124.035, 124.073), d(127.443, 127.527), d(129.849, 130.009), d(130.889, 130.943), d(160.167, 162.604) ppm; MS 343, 220, 109.

Compound 32: 2,6-cis-di-(m-fluorophenethyl)piperidine $^1$H NMR (300 MHz, $CDCl_3$) δ 1.07 (ddd, J=24.0, 13.2, 3.6 Hz, 2H), 1.33 (ddt, J=25.8, 12.9, 3.6 Hz, 1H), 1.58-1.75 (m, 6H), 1.80 (ddd, J=12.9, 6.3, 3.3 Hz, 1H), 2.50 (m, 2H), 2.64 (t, J=7.8 Hz, 4H), 6.83-7.00 (m, 6H), 7.23 (m, 2H) ppm; $^{13}$C NMR (75 MHz, $CDCl_3$) δ 24.9, 32.4, 32.8, 38.9, 56.7, d(112.645, 112.918), d(115.135, 115.409), d(124.065, 124.095), d(129.805, 129.912), d(144.855, 144.961), d(164.317, 164.567) ppm; MS 329, 206, 109.

Compound 33: N-methyl-2,6-cis-di-(m-fluorophenethyl)piperidine $^1$H NMR (300 MHz, $CDCl_3$) δ 1.33-1.50 (m, 5H), 1.65 (m, 2H), 1.78 (m, 1H) 1.84 (m, 2H), 2.15 (s, 3H), 2.37 (m, 2H), 2.67 (m, 4H), 6.84-6.94 (m, 4H), 6.97 (d, J=5.7 Hz, 2H), 7.22 (dt, J=4.5, 5.7 Hz, 2H) ppm; $^{13}$C NMR (75 MHz, $CDCl_3$) δ 25.2, 26.7, 30.3, 32.1, 36.1, 62.3, d(112.558, 112.770), d(115.351, 115.556), d(124.270, 124.293), d(129.781, 129.865), d(145.707, 145.775), d(161.883, 164.319) ppm; MS m/z 343, 220, 109 ($M^+$).

Compound 34:
2,6-cis-di-(p-fluorophenethyl)piperidine $^1$H NMR (300 MHz, CDCl$_3$) δ 1.08 (ddd, J=24.0, 12.9, 3.6 Hz, 2H), 1.33 (ddt, J=26.4, 12.9, 3.6 Hz, 1H), 1.58-1.74 (m, 6H), 1.80 (ddd, J=13.2, 5.7, 3.6 Hz, 1H), 2.49 (m, 2H), 2.61 (t, J=7.8 Hz, 4H), 6.96 (tt, J=9.0, 2.4 Hz, 4H), 7.12 (dd, J=9.0, 5.4 Hz, 4H) ppm; $^{13}$C NMR (75 MHz, CDCl$_3$) δ 25.0, 31.9, 32.9, 39.4, 56.8, 115.1, 115.4, 129.7, 129.8, 137.8, 137.9, 159.6, 162.9 ppm; MS m/z 329 (M$^+$).

Compound 35:
N-methyl-2,6-cis-di-(p-fluorophenethyl)piperidine $^1$H NMR (300 MHz, CDCl$_3$) δ 1.30-1.51 (m, 5H), 1.63 (m, 2H), 1.72-1.91 (m, 3H), 2.15 (s, 3H), 2.37 (m, 2H), 2.64 (m, 4H), 6.95 (tt, J=9.0, 2.4 Hz, 4H), 7.15 (dt, J=3.0, 9.0 Hz, 4H); $^{13}$C NMR (75 MHz, CDCl$_3$) δ 25.3, 26.8, 30.5, 31.7, 36.7, 62.4, d(114.9, 115.2), d(129.8, 129.9), 138.5, d(159.6, 162.8) ppm; MS m/z 343 (M$^+$).

Compound 36:
2,6-cis-di-(o-methoxyphenethyl)piperidine $^1$H NMR (300 MHz, CDCl$_3$) δ 1.09 (ddd, J=24.0, 12.6, 3.6 Hz, 2H), 1.29 (ddt, J=25.5, 12.6, 3.6 Hz, 1H), 1.58-1.76 (m, 6H), 1.76 (ddd, J=12.6, 6.3, 3.0 Hz, 1H), 2.45 (m, 2H), 2.65 (m, 4H), 3.79 (s, 6H), 6.82 (d, J=8.1 Hz, 2H), 6.87 (dt, J=7.5, 1.2 Hz, 2H), 7.10-7.20 (m, 4H) ppm; $^{13}$C NMR (75 MHz, CDCl$_3$) δ 25.0, 26.6, 32.8, 37.8, 55.3, 56.8, 110.2, 120.5, 127.0, 129.8, 130.7, 157.3 ppm;

Compound 37:
N-methyl-2,6-cis-di-(o-methoxyphenethyl)piperidine $^1$H NMR (300 MHz, CDCl$_3$) δ 1.36-1.56 (m, 5H), 1.64 (m, 2H), 1.74-1.90 (m, 3H), 2.21 (s, 3H), 2.35 (brs, 2H), 2.66 (t, J=8.4 Hz, 4H), 3.81 (s, 6H), 6.80-6.92 (m, 4H), 7.10-7.20 (m, 4H) ppm; $^{13}$C NMR (75 MHz, CDCl$_3$) δ 25.4, 27.2, 27.7, 31.8 34.9, 55.5, 63.4, 110.3, 120.5, 126.9, 129.9, 131.5, 157.5 ppm.

Compound 38:
2,6-cis-di-(m-methoxyphenethyl)piperidine.

$^1$H NMR (300 MHz, CDCl$_3$) δ 1.08 (ddd, J=24.0, 12.9, 3.6 Hz, 2H), 1.32 (ddt, J=25.8, 12.9, 3.6 Hz, 1H), 1.62-1.75 (m, 6H), 1.79 (ddd, J=13.2, 6.3, 3.0 Hz, 1H), 2.50 (m, 2H), 2.61 (t, J=8.1 Hz, 4H), 3.78 (s, 6H), 6.70-6.80 (m, 6H), 7.16-7.26 (m, 4H) ppm; $^{13}$C NMR (75 MHz, CDCl$_3$) δ 25.0, 32.8, 32.9, 39.1, 55.3, 56.9, 111.2, 114.2, 120.9, 129.4, 144.0, 159.7 ppm; MS m/z 353 (M$^+$).

Compound 39:
N-methyl-2,6-cis-di-(m-methoxyphenethyl)piperidine $^{13}$H NMR (300 MHz, CDCl$_3$) δ 1.40-1.62 (m, 3H), 1.73 (m, 2H), 1.82-1.95 (m, 3H), 2.17 (m, 2H), 2.50 (3, 3H), 2.67 (m, 4H), 3.81 (s, 6H), 6.73-6.82 (m, 6H), 7.21 (dd, J=9.0, 7.5 Hz, 2H) ppm; $^{13}$C NMR (75 MHz, CDCl$_3$) δ 22.8, 24.1, 32.4, 33.6, 55.6, 64.7, 112.4, 113.8, 120.7, 129.8, 141.2, 159.9 ppm; MS m/z 367 (M$^+$).

Compound 40:
2,6-cis-di-(p-methoxyphenethyl)piperidine $^1$H NMR (300 MHz, CDCl$_3$) δ 1.08 (ddd, J=23.7, 13.2, 3.3 Hz, 2H), 1.31 (ddt, J=25.8, 13.2, 3.3 Hz, 1H), 1.41 (brs, 1H), 1.58-1.73 (m, 6H), 1.78 (ddd, J=12.9, 6.3, 3.3 Hz, 1H), 2.48 (m, 2H), 2.57 (t, J=8.1 Hz, 4H), 3.77 (s, 6H), 6.82 (dd, J=8.7, 3.0 Hz, 4H), 7.09 (dd, J=8.7, 3.3 Hz, 4H) ppm; $^{13}$C NMR (75 MHz, CDCl$_3$) δ 25.0, 31.8, 32.9, 32.9, 39.4, 55.4, 56.8, 113.9, 129.3, 134.4, 157.8 ppm; MS m/z 353 (M$^+$).

Compound 41:
N-methyl-2,6-cis-di-(p-methoxyphenethyl)piperidine $^1$H NMR (300 MHz, CDCl$_3$) δ 1.40 (m, 4H), 1.55-1.70 (m, 3H), 1.70-1.90 (m, 3H), 2.16 (s, 3H), 2.37 (m, 2H), 2.60 (m, 4H), 3.78 (s, 6H), 6.82 (d, J=8.4 Hz, 4H), 7.12 (d, J=8.4 Hz, 4H) ppm; $^{13}$C NMR (75 MHz, CDCl$_3$) δ 25.4, 27.0, 30.9, 31.6, 36.9, 55.5, 62.6, 113.8, 129.4, 135.1, 157.6 ppm.

Compound 42:
2,6-cis-di-(p-methylphenethyl)piperidine $^1$H NMR (300 MHz, CDCl$_3$) δ 1.08 (ddd, J=24.0, 12.9, 3.3 Hz, 2H), 1.32 (m, 1H), 1.58-1.73 (m, 6H), 1.78 (m, 1H), 2.31 (s, 6H), 2.49 (m, 2H), 2.59 (t, J=8.1 Hz, 4H), 7.08 (s, 8H) ppm; $^{13}$C NMR (75 MHz, CDCl$_3$) δ 21.3, 25.1, 32.3, 32.9, 39.3, 56.9, 128.3, 129.2, 135.3, 139.3 ppm; MS m/z 321 (M$^+$).

Compound 43:
N-methyl-2,6-cis-di-(p-methylphenethyl)piperidine $^1$H NMR (300 MHz, CDCl$_3$) δ 1.26-1.48 (m, 5H), 1.63 (m, 2H), 1.75-1.92 (m, 3H), 2.16 (s, 3H), 2.31 (s, 6H), 2.36 (brt, J=6.0 Hz, 2H), 2.50-2.71 (m, 4H), 7.09 (s, 8H) ppm; $^{13}$C NMR (75 MHz, CDCl$_3$) δ 21.3, 25.3, 27.1, 31.0, 32.1, 36.8, 62.7, 128.4, 129.1, 135.1, 139.9 ppm; MS m/z 335 (M$^+$).

Compound 44:
2,6-cis-di-(m-trifluoromethylphenethyl)piperidine $^1$H NMR (300 MHz, CDCl$_3$) δ 1.08 (ddd, J=24.3, 12.9, 3.9 Hz, 2H), 1.35 (ddt, J=26.1, 12.9, 3.9 Hz, 1H), 1.61-1.78 (m, 6H), 1.82 (ddd, J=13.2, 6.3, 3.0 Hz, 1H), 2.52 (m, 2H), 2.71 (t, J=8.1 Hz, 4H), 7.34-7.58 (m, 8H) ppm; 13C NMR (75 MHz, CDCl$_3$) δ 24.9, 32.5, 32.9, 39.1, 56.7, q (118.961, 122.560, 126.174, 129.773), q (122.757, 122.803, 122.848, 122.909), q (125.081, 125.126, 125.187, 125.233), 128.9, q (130.138, 130.563, 130.988, 131.398), 131.8, 143.3 ppm.

Compound 45: N-methyl-2,6-cis-di-(m-trifluoromethylphenethyl)piperidine $^1$H NMR (300 MHz, CDCl$_3$) δ 1.39-1.57 (m, 5H), 1.67 (m, 2H), 1.74-1.96 (m, 3H), 2.17 (s, 3H), 2.42 (m, 2H), 2.75 (t, J=8.4 Hz, 4H), 7.36-7.50 (m, 8H) ppm; $^{13}$C NMR (75 MHz, CDCl$_3$) δ 25.4, 26.4, 29.7, 32.2, 36.2, 62.1, q (122.575, 122.621, 122.666, 122.727), q (125.233, 125.293, 125.339, 125.384), 126.2, 128.8, q (130.001, 130.411, 130.836, 131.261), 132.0, 143.8 ppm.

Compound 46:
2,6-cis-di-(p-phenylphenethyl)piperidine $^1$H NMR (300 MHz, CDCl$_3$) δ 1.11 (ddd, J=23.7, 12.6, 3.3 Hz, 2H), 1.34 (ddt, J=26.1, 3.3 Hz, 1H), 1.58-1.88 (m, 7H), 2.54 (m, 2H), 2.68 (t, J=7.8 Hz, 4H), 7.22-7.59 (m, 18H) ppm; $^{13}$C NMR (75 MHz, CDCl$_3$) δ 25.0, 32.3, 32.9, 39.1, 56.9, 127.0, 127.1, 127.2, 128.8, 128.9, 138.8, 141.1, 141.4 ppm.

Compound 47:
N-methyl-2,6-cis-di-(p-phenylphenethyl)piperidine $^{13}$H NMR (300 MHz, CDCl$_3$) δ 1.32-1.47 (m, 4H), 1.64-1.95 (m, 6H), 2.21 (s, 3H), 2.42 (m, 2H), 2.62-2.80 (m, 4H), 7.26-7.60 (m, 18H) ppm; $^{13}$C NMR (75 MHz, CDCl$_3$) δ 25.3, 26.9, 30.7, 32.0, 36.4, 62.6, 126.9, 127.2, 127.3, 128.9, 129.0, 138.8, 141.3, 142.3 ppm.

Compound 48:
2,6-cis-di-(p-hydroxymethylphenethyl)piperidine $^1$H NMR (300 MHz, CDCl$_3$) δ 1.26-1.46 (m, 3H), 1.64-1.85 (m, 3H), 1.85-2.06 (m, 4H), 2.41-2.66 (m, 4H), 2.92 (brs, 2H), 6.69 (dt, J=8.7, 2.5 Hz, 4H), 6.99 (dt, J=8.7, 2.4 Hz, 4H), 8.64 (m, 2H), 9.23 (s, 2H); $^{13}$C NMR (75 MHz, CDCl$_3$) δ 21.9, 27.4, 29.7, 34.8, 56.3, 115.0, 128.8, 130.6, 155.3 ppm.

Compound 49:
2,6-cis-di-(p-acetoxymethylphenethyl)piperidine $^1$H NMR (300 MHz, CDCl$_3$) δ 1.07 (ddd, J=23.4, 12.6, 3.6 Hz, 2H), 1.33 (ddt, J=25.8, 12.9, 3.6 Hz, 1H), 1.80 (ddd, J=10.2, 5.7, 3.0 Hz, 1H), 2.28 (s, 6H), 2.51 (m, 2H), 2.64 (t, J=7.8 Hz, 4H), 6.99 (dt, J=9.0, 2.4 Hz, 4H), 7.18 (dt, J=9.0, 2.4 Hz, 4H); $^{13}$C NMR (75 MHz, CDCl$_3$) δ 21.4, 24.9, 32.0, 32.8, 39.2, 56.8, 121.5, 129.3, 139.9, 148.8, 169.7 ppm.

Compound 50:
2,6-cis-di-(2,4-dichlorophenethyl)piperidine $^1$H NMR (300 MHz, CDCl$_3$) δ 1.09 (ddd, J=24.0, 12.6, 3.6 Hz, 2H), 1.35 (ddt, J=26.1, 12.9, 3.6 Hz, 1H), 1.56-1.77 (m, 6H), 1.83 (ddd, J=13.2, 6.6, 3.3 Hz, 1H), 2.53 (m, 2H), 2.74 (dd, J=10.7, 7.2 Hz, 4H), 7.15 (s, 2H), 7.16 (d, J=1.8 Hz, 2H), 7.35 (dd, J=1.8, 0.6 Hz, 2H); $^{13}$C NMR (75 MHz, CDCl$_3$) δ 24.9, 29.8, 32.7, 37.5, 56.8, 127.2, 129.3, 129.4, 131.1, 132.2, 134.6, 138.5 ppm.

Compound 51: N-methyl-2,6-cis-di-(2,4-dichlorophenethyl)piperidine $^1$H NMR (300 MHz, CDCl$_3$) δ 1.30-1.56 (m, 5H), 1.65 (m, 6H), 1.71-1.86 (m, 3 h), 2.18 (s, 3H), 2.38 (m, 2H), 2.66-2.84 (m, 4H), 7.14-7.22 (m, 4H), 7.35 (dd, J=1.8, 0.6 Hz, 2H); $^{13}$C NMR (75 MHz, CDCl$_3$) δ 25.3, 26.9, 29.8, 30.6, 34.4, 62.5, 127.1, 129.3, 131.4, 132.1, 134.6, 139.1 ppm.

Compound 52:
2,6-cis-di-(1-naphthalenethyl)piperidine $^1$H NMR (300 MHz, CDCl$_3$) δ 1.16 (ddd, J=23.4, 13.2, 3.3 Hz, 2H), 1.39 (ddt, J=26.4, 13.2, 3.3 Hz, 1H), 1.72-1.92 (m, 7H), 2.63 (m, 2H), 3.09 (dd, J=9.0, 6.3 Hz, 4H), 7.29-7.42 (m, 4H), 7.42-7.53 (m, 4H), 7.70 (d, J=7.8 Hz, 2H), 7.84 (dd, J=7.2, 2.4 Hz, 2H), 8.04 (d, J=7.5 Hz, 2H); $^3$C NMR (75 MHz, CDCl$_3$) δ 25.1, 29.9, 32.9, 38.6, 57.4, 124.0, 125.6, 125.7, 125.9, 126.0, 126.7, 128.9, 131.9, 134.0, 138.5 ppm.

Compound 53:
N-methyl-2,6-cis-di-(1-naphthalenethyl)piperidine $^1$H NMR (300 MHz, CDCl$_3$) δ 1.40-1.64 (m, 4H), 1.68-1.90 (m, 4H), 2.03 (m, 2H), 2.24 (s, 3H), 2.61 (m, 2H), 3.18 (t, J=8.1 Hz, 4H), 7.34-7.41 (m, 4H), 7.42-7.54 (m, 4H), 7.71 (dd, J=6.3, 2.7 Hz, 2H), 7.85 (dd, J=7.5, 1.5 Hz, 2H), 8.11 (d, J=8.1 Hz, 2H); $^{13}$C NMR (75 MHz, CDCl$_3$) δ 25.3, 26.7, 29.6, 30.5, 35.8, 63.1, 124.0, 125.5, 125.7, 125.9, 126.1, 126.6, 128.9, 132.0, 134.0, 139.1 ppm.

Compound 54:
2,6-cis-di-(2-naphthalenethyl)piperidine $^1$H NMR (300 MHz, CDCl$_3$) δ 1.12 (ddd, J=23.7, 12.9, 3.0 Hz, 2H), 1.39 (ddt, J=25.8, 12.9, 3.6 Hz, 1H), 1.60-1.86 (m, 7H), 2.52 (m, 2H), 2.77 (t, J=7.8 Hz, 4H), 7.30 (dd, J=8.7, 1.2 Hz, 2H), 7.36-7.47 (m, 4H), 7.58 (brs, 2H), 7.71-7.82 (m, 6H); $^{13}$C NMR )75 MHz, CDCl$_3$) δ 25.0, 32.8, 32.9, 39.0, 56.9, 125.2, 126.0, 126.4, 127.4, 127.5, 127.7, 128.0, 132.1, 133.7, 139.8 ppm.

Compound 55:
N-methyl-2,6-cis-di-(2-naphthalenethyl)piperidine $^1$H NMR (300 MHz, CDCl$_3$) δ 1.33-1.45 (m, 4H), 1.70-1.83 (m, 4H), 2.02 (m, 2H), 2.23 (s, 3H), 2.48 (m, 2H), 2.85 (m, 4H), 7.35 (dd, J=6.6, 1.5 Hz, 2H), 7.38-7.46 (m, 4H), 7.65 (brs, 2H), 7.74-7.82 (m, 6H) ppm; 13C NMR (75 MHz, CDCl$_3$) δ 25.2, 29.7, 30.1, 32.9, 36.5, 64.1, 125.9, 126.1, 126.5, 127.6, 127.7, 127.8, 128.2, 131.9, 133.6, 139.7 ppm.

EXAMPLE 19

Preparation of Compounds 56 and 57

Compound 56 and 57 were prepared as illustrated in Scheme 2 by the similar procedure as described in Scheme 1 above.

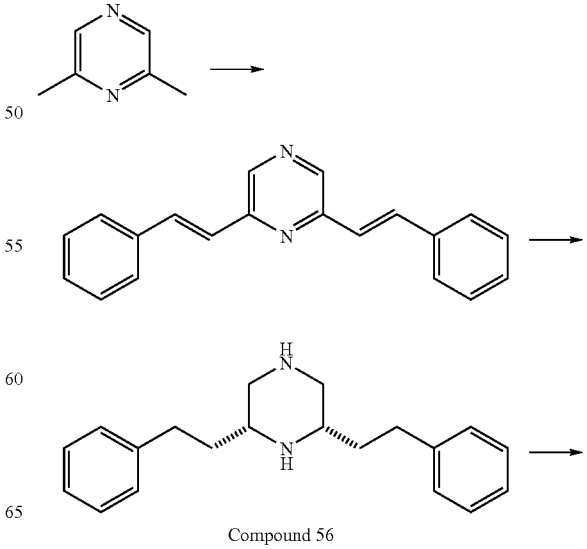

Scheme 2

Compound 56

-continued

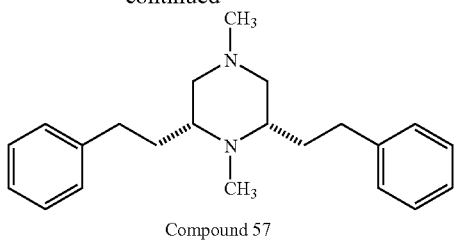

Compound 57

Compound 56: 2,6-cis-diphenethylpiperazine

¹HNMR (300 MHz, DMSO-d6) δ 7.14-7.40 (m, 10H), 3.36-3.72 (m, 4H), 3.14 (t, J=12.3 Hz, 2H), 2.62-2.85 (m, 4H), 2.13 (m, 2H), 1.96 (m, 2H) ppm; ¹³CNMR (75 MHz, DMSO-d6) δ 30.2, 31.4, 43.0, 52.0, 126.0, 128.1, 128.3, 140.2 ppm.

Compound 57: 1,4-dimethyl-2,6-cis-diphenethylpiperazine

¹HNMR (300 MHz, CDCl₃) δ 7.13-7.39 (m, 10H), 2.55-2.83 (m, 6H), 2.40 (m, 2H), 2.30 (s, 3H), 2.25 (s, 3H), 2.01 (t, J=11.4 Hz, 2H), 1.93 (m, 2H), 1.70 (m, 2H) ppm; ¹³CNMR (75 MHz, CDCl₃) δ 32.2, 33.8, 35.7, 46.3, 58.9, 61.9, 125.9, 128.3, 128.4, 142.3 ppm.

EXAMPLE 20

Preparation of Compounds 58 and 59: 2,6-cis-2-phenethynyl-6-phenethylperidin-4-one and 2,6-trans-2-phenethynyl-6-phenethylperidin-4-one TrocCl (9.26 g, 43.71 mmol) was added dropwise at −30° C. to a solution of 4-methoxypyridine (4.77 g, 43.71 mmol) in 60 mL THF. The resulting mixture was stirred for 30 min at −30° C., and Phenylethynylmagnesium bromide (1M in THF, 65 mL) was added through a syringe. The mixture was stirred at −20° C. for 2 hours. 1M HCl (50 mL) was then added, and the mixture was stirred at room temperature for 30 min and diluted with water (150 mL). The mixture was extracted with ethylacetate (3×100 mL). The combined organic layers were washed with brine (100 mL), dried over Na₂SO₄, filtered, and concentrated. The crude product was purified by column chromatography (10:1 hexanes:ethylacetate) on silica gel to a white solid, yield: 76%.

Phenylethylmagnesium bromide (1M in THF, 25 mL) was added to a solution of CuBr.SMe₂ (5.14 g, 25 mmol) in 50 mL THF at −25° C. The resulting mixture was stirred at −20° C. to −30° C. for 15 min, and then cooled to −78° C. To the mixture was added boron trifluoride etherate (1.27 mL, 10 mmol). After 30 min, above product white solid (3.73 g, 10 mmol) in 30 mL THF was added dropwise to the mixture. The mixture was stirred at −78° C. for 3 h and then poured into aqueous 20% NH₄Cl/NH₄OH (50:50) solution (400 mL). The aqueous layer was extracted with ethylacetate (3×150 mL). The combined organic layers were washed with brine (100 mL), dried over Na₂SO₄, filtered, and concentrated. The crude product was purified by column chromatography (6:1 hexanes:ethylacetate) on silica gel to give Troc protected compound 58 (3.09 g, 64.5%) and 59 (530 mg, 11%) as white solids. These compounds were deprotected under Zn/HOAc at room temperature for 4 h to give the title compound 58 and 59, respectively.

Compound 58: 2,6-cis-2-phenethynyl-6-phenethylperidin-4-one

¹H NMR (300 MHz, CDCl₃) δ 1.76-1.98 (m, 2H), 2.18 (dd, J=13.8, 12.0 Hz, 1H), 2.46 (ddd, J=13.8, 2.7, 1.8 Hz, 1H), 2.54-2.78 (m, 4H), 2.87 (m, 1H), 3.90 (dd, J=11.7, 4.2 Hz, 1H), 7.05-7.50 (m, 10H) ppm; MS m/z 302 (M⁺−1).

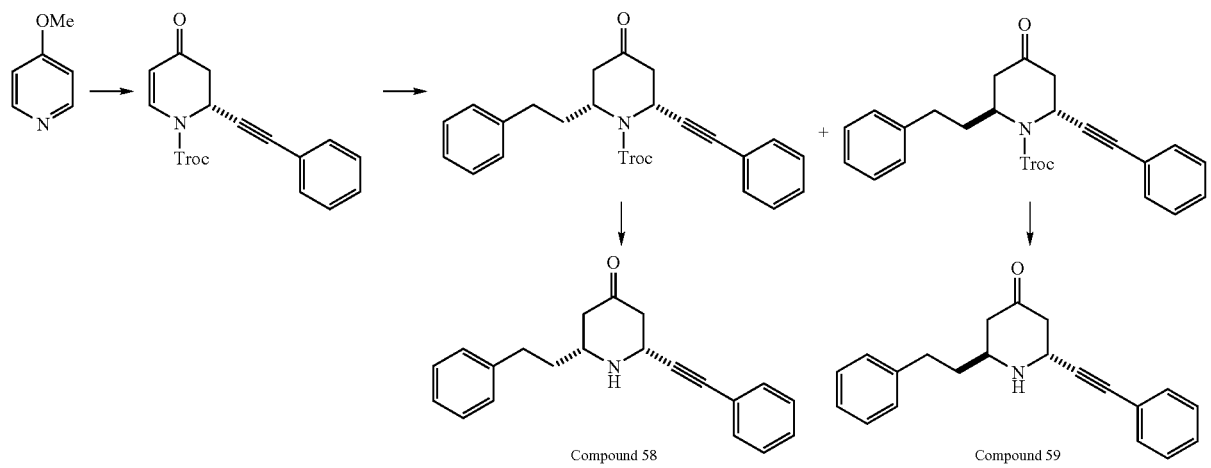

Compound 58                Compound 59

Compound 59: 2,6-trans-2-phenethynyl-6-phenethylperidin-4-one

¹H NMR (300 MHz, CDCl₃) δ 1.75-1.95 (m, 2H), 2.22 (dd, J=14.1, 11.1 Hz, 1H), 2.52 (ddt, J=21.9, 14.1, 2.4 Hz, 2H), 2.71 (t, J=7.8 Hz, 2H), 2.79 (dd, J=14.1, 6.3 Hz, 1H), 3.53 (m, 1H), 4.55 (dd, J=6.3, 2.4 Hz, 1H), 7.12-7.39 (m, 10H) ppm; ¹³C NMR (75 MHz, CDCl₃) δ 32.2, 38.4, 46.8, 47.0, 48.5, 51.7, 86.4, 88.1, 122.5, 126.2, 128.3, 128.49, 128.53, 128.7, 131.9, 141.3, 206.8 ppm; MS m/z 303 (M⁺).

EXAMPLE 21

High Affinity [$^3$H]Nicotine Binding Assay

The ability to displace S(-)[$^3$H]nicotine (NIC) binding from rat striatal membranes to assess interaction with the α4β2* subtype was determined. The [$^3$H]NIC binding assay was performed according to previously published methods (Romano et al., 1980; Marks et al., 1986; Crooks et al., 1995). Striata from two rats were dissected, pooled and homogenized with a Tekmar polytron in 10 vol of ice-cold modified Krebs-HEPES buffer (in mM; 20 HEPES, 118 NaCl, 4.8 KCl, 2.5 CaCl$_2$, 1.2 MgSO$_4$, adjusted to pH to 7.5). The homogenate was incubated at 37° C. for 5 minutes to promote hydrolysis of endogenous acetylcholine, and centrifuged at 15,000 g for 20 minutes and the pellet was resuspended in 10 vol of ice-cold distilled water and incubated at 37° C. for 5 minutes, followed by centrifugation at 15,000 g for 20 min. The pellet containing the striatal membranes was resuspended in 10 vol of fresh ice-cold 10% Krebs-HEPES buffer and incubated at 37° C. for 10 min after which it was centrifuged at 15,000 g for 20 minutes. The latter sequence of resuspension, incubation and centrifugation was repeated. The pellet was frozen under fresh Krebs-HEPES buffer and stored at −40° C. until assay. Upon assay, the pellet was resuspended in Krebs-HEPES buffer, incubated at 37° C. for 5 minutes and centrifuged at 15,000 g for 20 minutes. The final pellet was resuspended in 3.6 ml ice-cold water which provides for approximately 200 μg protein/100 μl aliquot. Competition assays were performed in duplicate in a final volume of 200 μl Krebs-HEPES buffer containing 250 mM Tris buffer (pH 7.5 at 4° C.). Reactions were initiated by addition of 100 μl of membrane suspension to 3 nM [$^3$H]NIC (50 μl) and 1 of at least 9 concentrations of analog (50 μl). After 90 minutes incubation at 4° C., reactions were terminated by dilution of the samples with 3 ml of ice-cold buffer followed immediately by filtration through a Whatman GF/B glass fiber filters (presoaked in 0.5% polyethyleneimine (PEI) using a Brandel Cell Harvester. Filters were rinsed 3× with 3 ml of ice-cold buffer, transferred to scintillation vials and 5 ml scintillation cocktail added. Nonspecific binding was defined as binding in the presence of 10 μM NIC. For competition curves, the IC$_{50}$ values were corrected for ligand concentration (Cheng and Prusoff, 1973).

EXAMPLE 22

[$^3$H]Dopamine ([$^3$H]DA) Uptake Assay, Striatal Synaptosomal Preparation

[$^3$H]DA uptake was performed according to a modification of the previously reported methods (Dwoskin et al., 1999). Striata were homogenized in 20 ml of ice-cold sucrose solution (0.32 M sucrose and 5 mM sodium bicarbonate, pH 7.4) with 12 passes of a teflon-pestle homogenizer (clearance approximately 0.003 in). The homogenate was centrifuged at 2,000 g, 4° C. for 10 min. The supernatant was centrifuged at 12,000 g, 4° C. for 20 minutes. The resulting pellet was resuspended in 1.5 ml ice-cold assay buffer (in mM; 125 NaCl, 5 KCl, 1.5 KH$_2$PO$_4$, 1.5 MgSO$_4$, 1.25 CaCl$_2$, 10 glucose, 0.1 L-ascorbate, 25 HEPES, 0.1 EDTA and 0.1 pargyline; pH 7.4). The final protein concentration was 400 Hg/ml. Assays were performed in duplicate in a total vol of 500 μl. Aliquots (50 μl synaptosomal suspension containing 20 μg of protein) were added to assay tubes containing 350 μl buffer and 50 μl of 1 of 9 concentrations (final concentration, 1 nM-1 mM) of analog or vehicle. Synaptosomes were preincubated at 34° C. for 10 min before the addition of 50 μl of [$^3$H]DA (30.1 Ci/mmole, final concentration 100 nM) and accumulation proceeded for 10 min at 34° C. High affinity uptake was defined as the difference between accumulation in the absence and presence of 10 μM GBR 12935. Preliminary studies demonstrated that at 10 minutes [$^3$H]DA uptake is within the linear range of the time-response curve when experiments are performed at 34° C. Accumulation was terminated by addition of 3 ml ice-cold assay buffer containing 1 mM pyrocatechol and rapid filtration through a Whatman GF/B glass fiber filter paper (presoaked with buffer containing 1 mM pyrocatecol) using a Brandel Cell Harvester. The filters were washed 3 times with 3 ml of 10 ml ice-cold buffer containing 2 mM pyrocatechol, and then transferred to scintillation vials and radioactivity determined (Packard Model B1600TR scintillation counter, Meriden, Conn.). Protein concentration was determined using bovine serum albumin as the standard (Bradford, 1976). Competition curves for analog inhibition of [$^3$H]DA uptake were generated. Non-linear regression analysis was used to fit curves either in the absence or presence of 9 concentrations of analog. IC50 values were corrected for concentration of [$^3$H]DA (Cheng and Prusoff, 1973) to yield true inhibition constants (Ki=IC50/[1+c/Km]), where c is the concentration of free [$^3$H]DA and Km is the concentration of analog at which half maximal [$^3$H]DA uptake is achieved. These values (Ki) were converted to pKi before statistical analysis.

EXAMPLE 23

[$^3$H]Methyllycaconitine ([$^3$H]MLA)Binding Assay

Whole rat brain (minus cortex, striatum and cerebellum) was homogenized in 20 vol of ice-cold hypotonic buffer (2 mM HEPES, 14.4 mM NaCl, 0.15 mM KCl, 0.2 mM CaCl$_2$ and 0.1 mM MgSO$_4$, pH 7.5). Homogenates were incubated at 37° C. for 10 min and centrifuged at 25,000 g for 15 min at 4° C. Pellets were washed 3 times by resuspension in 20 vol of the same buffer and centrifugation using the above parameters. Final pellets were resuspended in incubation buffer to provide ~150 μg protein/100 μL. Binding assays were performed in duplicate, in a final vol of 250 μL incubation buffer, containing 20 mM HEPES, 144 mM NaCl, 1.5 mM KCl, 2 mM CaCl$_2$, 1 mM MgSO$_4$ and 0.05% BSA, pH 7.5. Assays were initiated by the addition of 100 μL membrane suspension to 150 μL of sample containing 2.5 nM [$^3$H]MLA ([1α, 4(S), 6β, 14α, 16β]-20-ethyl-1,6,14,16-tetramethoxy-4[[[2-(-[3-$^3$H]-methyl-2,5-dioxo-1-pyrrolidinyl)benzoyl]oxy]methyl]aconitane-7,8-diol; specific activity 26.2 Ci/mMol) and at least 6 concentrations (30 nM-100 μM) synthetic analog (final concentrations), and incubated for 2 h at room temperature. Nonspecific binding was determined in the presence of 10 μM MLA. Assays were terminated by dilution of samples with 3 mL ice-cold incubation buffer followed by immediate filtration through Schleicher & Schuell #32 glass fiber filters (Keene, N.H.; presoaked with 0.5% PEI) using the cell harvester. Filters were rinsed 3 times with 3 mL of ice-cold buffer, transferred to scintillation vials, 4 mL of scintillation cocktail added, and bound radiolabel determined by liquid scintillation spectroscopy. Protein was measured using the Bradford dye-binding method (Bradford, 1976) with BSA as the standard.

EXAMPLE 24

[$^3$H]Methoxytetrabenazine [$^3$H]MTBZ Binding Assay and [$^3$H]Dihydrotetrabenazine [$^3$H]DTBZ Binding Assay Synaptic vesicles were prepared from rat brain using a modification of a previously described procedure (Teng et al., 1998). Briefly, fresh whole brain (excluding cerebellum) was homogenized using a Teflon pestle (clearance 0.003 mm) with 7 vertical strokes at 800 rpm in 20 vol of ice-cold 0.32 M sucrose and centrifuged at 1000 g for 12 min at 4° C. The resulting supernatant ($S_1$) was then centrifuged at 22,000 g for 10 min at 4° C. The synaptosomal pellets ($P_2$) were homogenized in 18 mL of ice-cold Milli-Q water and exposed for 5 min for lysing synaptosomes. Osmolarity was restored by addition of 2 mL of 25 mM HEPES with 100 mM dipotassium tartrate (pH 7.5). Samples were centrifuged at 20,000 g for 20 min at 4° C. to remove lysed synaptosomal membranes. $MgSO_4$ (1 mM) was added to the supernatant ($S_3$), and was centrifuged at 100,000 g for 45 min at 4° C. The final vesicular pellets ($P_4$) were resuspended in ice-cold assay buffer (see below) providing ~15 µg protein/100 µL, determined by the method of Bradford (1976) using bovine serum albumin as a standard. Aliquot parts (100 µL) of suspension of vesicle membrane protein were incubated in assay buffer (25 mM HEPES, 100 mM dipotassium tartrate, 5 mM $MgSO_4$, 0.1 mM EDTA and 0.05 mM EGTA, pH 7.5, at 25° C.) in the presence of 3 nM [$^3$H]MTBZ ([O-methyl-$^3$H]methoxytetrabenazine) or [$^3$H]DTBZ ([$^3$H] dihydrotetrabenazine) and at least 7 concentrations (1 nM-1 mM) of analog for 1 hr at room temperature. Nonspecific binding was determined in the presence of 20 µM TBZ or 10 µM Ro41283. Assays were performed in duplicate using a 96-well plate format. Reactions were terminated by filtration of samples on a Unifilter-96 GF/B filter plates (presoaked in 0.5% polyethylenimine), using a FilterMate harvester (Packard BioScience Co., Meriden, Conn.). After washing 5 times with 350 µL of the ice-cold wash buffer (25 mM HEPES, 100 mM dipotassium tartrate, 5 mM $MgSO_4$ and 10 mM NaCl, pH 7.5), filter plates were dried, sealed and each well filled with 40 µL Packard's MicroScint 20 cocktail. Bound [$^3$H]MTBZ or [$^3$H]DTBZ was measured using a Packard TopCount NXT scintillation counter with a Packard Windows NT based operating system.

EXAMPLE 25

[$^3$H]5-HT Uptake Assay

[$^3$H]5-HT uptake was assessed using modifications of a previously described method (Teng et al., 1998). Nonspecific uptake was determined in duplicate samples in the presence of excess (10 µM) fluoxetine. Rat hippocampus was homogenized in 20 mL cold 0.32 M sucrose containing 5 mM $NaHCO_3$ (pH 7.4) with 12 vertical strokes of a Teflon pestle homogenizer (clearance ~0.015 mm). The homogenate was centrifuged (2,000×g for 10 min at 4° C.). The supernatant was centrifuged (20,000×g for 15 min at 4° C.), and then the pellet was resuspended in 1.5 mL of Kreb's buffer (125 mM NaCl, 5 mM KCl, 1.5 mM $MgSO_4$, 1.25 mM $CaCl_2$, 1.5 mM $KH_2PO_4$, 10 mM α-D-glucose, 25 mM HEPES, 0.1 mM disodium ethylenediamine tetraacetate, 0.1 mM pargyline and 0.1 mM ascorbic acid, saturated with 95% $O_2$/5% $CO_2$, pH 7.4). Final protein concentration was 400 µg/mL, determined using BSA standard (Bradford, 1976). The assay was performed in duplicate in a total vol of 500 µL. Aliquot parts of synaptosomal. suspension (50 µL) were added to tubes containing 350 µL Kreb's buffer and 50 µL of buffer containing 1 of 9 concentrations of analog. Tubes were preincubated at 34° C. for 10 min before addition of 50 µL of [$^3$H]5-HT (5-[1,2-$^3$H(N)]-hydroxytryptamine; specific activity 25.5 Ci/mMol, final concentration 10 nM). Accumulation proceeded for 10 min at 34° C. Reactions were terminated by addition of 3 mL ice-cold Kreb's buffer. Samples were rapidly filtered through a Whatman GF/B filter using a cell harvester (MP-43RS, Brandel Inc., Gaithersburg, Md.), and the filter was subsequently washed 3 times with 4 mL ice-cold Kreb's buffer containing catechol (1 mM). Filters were previously soaked for 2 hours in the ice-cold Kreb's buffer containing catechol (1 mM). Radioactivity on filters was determined by liquid scintillation spectroscopy.

EXAMPLE 26

Endogenous Dopamine (DA), [$^3$H]DA and [$^3$H]Norepinephrine (NE) Release Assays Alkaloid effects on either endogenous or [$^3$H]overflow from rat striatal slices (for DA release) and rat hippocampal slices (for NE release) were determined using modifications of a previously published method (Dwoskin and Zahniser, 1986). Briefly, coronal striatal or hippocampal slices (500 µm, 6-8 mg) were incubated in Krebs' buffer (118 mM NaCl, 4.7 mM KCl, 1.2 mM $MgCl_2$, 1.0 mM $NaH_2PO_4$, 1.3 mM $CaCl_2$, 11.1 mM α-D-glucose, 25 mM $NaHCO3$, 0.11 mM L-ascorbic acid and 4.0 mM disodium ethylenediaminetetraacetate; pH 7.4, and saturated with 95% $O_2$/5% $CO_2$) in a metabolic shaker at 34° C. for 30 min. For the radiolabelled-neurotransmitter release assays, either striatal or hippocampal slices were incubated in fresh buffer (6-8 slices/3 mL) containing 0.1 µM [$^3$H]DA (3,4-[7-$^3$H]-dihydroxyphenylethylamine; specific activity 28 Ci/mMol) or 0.1 µM [$^3$H]NE (levo-[7-$^3$H]-norepinephrine; specific activity 14.4 Ci/mMol), respectively, for an additional 30 min. For the endogenous DA superfusion assay, striatal slices were incubated for an additional 30 min in the absence of exogenous transmitter. After rinsing, each slice was transferred to a glass superfusion chamber maintained at 34° C. and was superfused at 1 mL/min with oxygenated Krebs' buffer. In the radiolabelled neurotransmitter release assays, the Krebs buffer contained pargyline (10 µM) and nomifensine (10 µM) or pargyline and desipramine (10 µM) in experiments assessing [$^3$H]DA and [$^3$H]NE overflow, respectively, to prevent retake of radiolabeled neurotransmitter following release. In the endogenous DA release assay, neither of these inhibitors was used and both DA and its major metabolite (dihydroxyphenylacetic acid, DOPAC) were assessed in the superfusate. After 60 min of superfusion, three 5-min samples (5 mL) were collected to determine basal endogenous DA outflow or [$^3$H]neurotransmitter outflow, respectively. After collection of the third basal sample, slices from an individual rat were superfused in the absence or presence of a single concentration of analog, which remained in the buffer until the end of the experiment. Each slice was exposed to only one concentration of analog. In some experiments, after 30 min, S(−)-nicotine (10 µM) was added to the buffer containing analog, and superfusion continued for an additional 60 min. In endogenous DA release assays, methamphetamine (5 µM) was added to the buffer for 15 min followed by superfusion in its absence for another 20 min. These experiments utilized a repeated measures design, such that the analog concentration-effect was determined in both the absence and presence of S(−)-nicotine using striatal or hippocampal slices from a single rat or of methamphetamine using striatal slices from a single rat. Additionally, one striatal or hippocampal slice was superftised in the absence of analog and constituted the nicotine control condition or the methamphetamine control condition, respectively. At the end of the experiment, each slice from the radiolabelled neurotransmitter release assays was solubilized with TS-2. The pH and volume of the solubilized tissue samples were adjusted to those of the superfusate samples. Radioactivity in the superfusate and tissue samples was determined by liquid scintillation spectroscopy (Packard model B1600 TR Scintillation Counter, Downer's Grove, Ill.). At the end of the endogenous DA release assays, striatal slices were placed in 0.1 M perchoric acid and stored in a −70° C. freezer until analysis of tissue levels of DA and DOPAC by high pressure liquid chromatography. An aliquot part (500 µl) of each 1-ml superfusate sample was added to 20 µl of ascorbate oxidase (17 activity units/ml) and was then injected onto the high pressure liquid chromatography with electrochemical detection system, which consisted of a Beckman model 116 high pressure liquid chromatography pump (Beckman, Fullerton Calif.), a Beckman model 508 autosampler, an ESA ODS ultrasphere C18 reverse-phase colum (4.6 cm×75 mm, 3-µm particle size; ESA, Bedford, Mass.), and an ESA coulometric-II electrochemical detector with a model 5011 detector cell (E1=−0.05 V, E2=+0.32 V) and model 5020 guard cell (+0.60 V). The eluent was 0.07 M citrate/0.1 M acetate buffer (pH 4) containing, 175 mg/l octylsulfonic acid-sodium salt, 650 mg/l of NaCl and 7% methanol. All separations were performed at room temperature at a flow rate of 1.5 ml/min. Complete separation of DA and DOPAC and re-equilibration of the system required 5-6 min. Retention times of DA and DOPAC standards were used to identify relevant peaks. Peak heights were used to calculate detected amounts on the basis of standard curves. The detection limits were about 1 and 2 pg/ml for DA and DOPAC, respectively.

EXAMPLE 27

$^{86}Rb^+$ Rubidium Efflux Assay

Analog effects on $^{86}Rb^+$ efflux were determined using a previously published method (Miller et al., 2000). Thalamus was homogenized and centrifuged at 1000×g for 10 min at 4° C. The supernatant fraction was centrifuged at 12,000×g for 20 min at 4° C. to obtain the synaptosomal fraction. Synaptosomes were incubated for 30 min in 35 µL of uptake buffer (140 mM NaCl, 1.5 mM KCl, 2.0 mM $CaCl_2$, 1.0 mM $MgSO_4$, 20 mM α-D-glucose; pH 7.5) containing 4 µCi of $^{86}Rb^+$. $^{86}Rb^{30}$ uptake was terminated by filtration of the synaptosomes onto glass fiber filters (6 mm; Type A/E, Gelman Sciences, Ann Arbor, Mich.) under gentle vacuum (0.2 atm), followed by three washes with superfusion buffer (0.5 mL each). Subsequently, each filter with $^{86}Rb^{30}$-loaded synaptosomes (40 µg protein/µl) was placed on a 13 mm glass fiber filter (Type A/E) mounted on a polypropylene platform. $^{86}Rb^{30}$ efflux assay buffer (125 mM NaCl, 5 mM CsCl, 1.5 mM KCl; 2 mM $CaCl_2$, 1 mM $MgSO_4$, 25 mM HEPES, 20 mM α-D-glucose, 0.1 µM tetrodotoxin, 1.0 g/L bovine serum albumin; pH 7.5) was superfused onto the synaptosomes at a rate of 2.5 mL/min. Tetrodotoxin and CsCl were included in the buffer to block voltage-gated $Na^+$ and $K^+$ channels, respectively, and to reduce the rate of basal $^{86}Rb^{30}$ efflux. The ability of analogs to inhibit $^{86}Rb^{30}$ efflux evoked by 1 M nicotine was determined. After 8 min of superfusion, samples were collected (sample/18 s) for 5 min to determine basal $^{86}Rb^{30}$ efflux. Subsequently, synaptosomes were superfused for 3 min with analog followed by superfusion with buffer containing analog and nicotine for an additional 3 min. Each aliquot part of thalamic synaptosomes was exposed to only one concentration of analog. In each experiment, one synaptosomal aliquot part was superfused in the absence of analog to determine basal $86Rb^{30}$ efflux over the course of the superfusion period, and another aliquot part was superfused with nicotine (1 µM) to determine the effect of nicotine on $^{86}Rb^{30}$ efflux in the absence of analog. Samples were analyzed by liquid scintillation spectroscopy (Packard model B1600 TR Scintillation Counter).

In the examples listed in Tables 1 and 2, a series of 2,6-disubstituted piperidines and 2,6-disubstituted piperazino analogs, structurally related to lobeline, were synthesized and tested for activity in the nicotinic receptor assays and dopamine transporter and release assays to assess the interaction of these piperidines and piperazines with these specific proteins on the presynaptic terminal of monoaminergic neurons in the CNS. Some of these compounds have greater selectivity for interaction with DAT than for interaction with nicotinic receptors, whereas other compounds interact with both nicotinic receptors and DAT, more similar to lobeline. Other compounds were more selective for the nicotinic receptor than for DAT. These combinations of pharmacological activity are considered to be beneficial for the treatment of psychostimulant abuse and withdrawal, eating disorders, and central nervous system diseases and pathologies.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalence thereof may be resorted to, falling within the scope of the invention claimed.

REFERENCES

The pertinent disclosures of the references listed below and as discussed above herein are incorporated herein by reference.

Barlow R. B. et al., "Relations between structure and nicotine-like activity: X-ray crystal structure analysis of (−)cystine and (−)lobeline hydrochloride and a comparison with (−) nicotine and other nicotine-like compounds," *Br. J. Pharmacol.*, 1989; 98: 799-808.

Bradford M M, "A rapid and sensitive method for the quantitation of microgram quantities of protein utilizing the principle of protein-dye binding. *Ann. Biochem.*, 1976; 72: 248-253.

Broussolle E. P. et al., "In vivo binding of $^3H$-nicotine in the mouse brain," *Life Sciences,* 1989; 44: 1123-1132.

Cheng Y. C. and Prusoff W., "Relationship between the inhibition constant ($K_i$) and the concentration of inhibitor which causes 50 percent inhibition ($I_{50}$) of an enzymatic reaction," *Biochem. Pharmacol.*, 1973; 22: 3099-3108.

Clarke P. B. S. et al., "Release of [$^3H$]noradrenaline from rat hippocampal synaptosomes by nicotine: mediation by different nicotinic receptor subtypes from striatal [$^3H$] dopamine release," *Br. J. Pharmacol.*, 1993; 45: 571-576.

Crooks P. A. et al., "Inhibition of nicotine-evoked dopamine release by pyridino-N-substituted nicotine analogues: a new class of nicotinic antagonist," *Drug Dev. Res.*, 1995; 36: 71-82.

Decker M. W. et al., "Effects of lobeline, a nicotinic receptor agonist, on learning and memory," *Pharmacol. Biochem. Behav.* 1993; 45: 571-576.

Dwoskin L. P. and Zahniser N. R., "Robust modulation of [$^3$H]dopamine release from rat striatal slices by D-2 dopamine receptors. *J. Pharmacol. Exp. Ther.* 1986; 239: 442-453.

Dwoskin L. P. et al., "S-(–)-Cotinine, the major brain metabolite of nicotine, stimulates nicotinic receptors to evoke [$^3$H]dopamine release from rat striatal slices in a calcium-dependent manner," *J. Pharmacol. Exp. Therap.*, 1999; 288: 905-911.

Ebnöther, A.; Über die Mutarotation des Lobelins. Cis-trans-Isomere in der Reihe der Lobelia-Alkaloide. *Helv. Chim. Acta* 1958, 41, 386-396.

Hamann S. R. et al., "Hyperalgesic and analgesic actions of morphine, U50-488, naltrexone, and (–)lobeline in the rat brainstem," *Pharmacol. Biochem. Behav.*, 1994; 47: 197-201.

Lippiello P. M. et al., "The binding of L-[$^3$H]nicotine to a single class of high affinity sites in rat brain membrane," *Mol. Pharmacol.*, 1986; 29: 448-454.

Marks M. J. et al., "Nicotine binding sites in rat and mouse brain: comparison of acetylcholine, nicotine and α-bungarotoxin," *Mol. Pharmacol.*, 1986; 30: 427-436.

Miller D. K et al., "Lobeline inhibits nicotine-evoked [$^3$H]dopamine overflow from rat striatal slices and nicotine-evoked $^{86}$Rb$^{30}$ efflux from thalamic synaptosomes. *Neuropharmacology*, 2000; 39:2654-2662.

Olin B. R. et al., *Drug Facts and Comparisons*, J B Lippincott Co., St. Louis, Mo., pp 3087-3095 (1995).

Romano C. et al., "Stereospecific nicotinic receptors on rat brain membranes," *Science*, 1980; 210: 647-650.

Teng L. H. et al., "Lobeline and nicotine evoke [$^3$H]-overflow from rat striatal slices preloaded with [$^3$H]dopamnine: differential inhibition of synaptosomal and vesicular [$^3$H]dopamine uptake," *J. Pharmacol. Exp. Therap.*, 1997; 80: 1432-1444.

Teng L. H. et al, "Lobeline displaces [$^3$H]dihydrotetrabenazine binding and releases [$^3$H]dopamine from rat sriatal synaptic vesicles," *J. Neurochem.*, 1998; 71: 258-265.

What is claimed is:

1. A 2,6-substituted piperidino compound or pharmaceutically effective salts thereof, including resolved diasteriomers or enantiomers thereof, comprising the following formula:

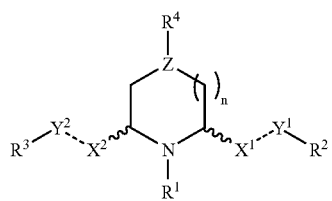

wherein
n is an integer from 0 to 3;
X$^1$ represents CH$_2$;
Y$^1$ represents CHOH or C=O;
X$^2$—Y$^2$ represents a cis-carbon-carbon double bond or a trans-carbon-carbon double bond;
Z represents CH;
R$^1$ and R$^4$ are the same or independently different from one another and represent hydrogen or a lower straight chain or branched alkyl;
R$^2$ and R$^3$ are the same or are independently different from one another and represent a saturated or unsaturated hydrocarbon ring, or an ortho, meta or para-substituted benzene.

2. The compound of claim 1, wherein R$^2$ and R$^3$ are benzene rings.

3. The compound of claim 2, wherein R$^1$ is hydrogen, methyl, ethyl or propyl.

4. The compound of claim 1, wherein R$^2$ and R$^3$ are substituted benzenes containing at least one substituent selected from the group consisting of methyl, ethyl, propyl, isopropyl, butyl, sec-butyl, isobutyl, carboxaldehyde, acetoxy, propionyloxy, isopropionyloxy, acetyl, propionyl, formyl, benzoyl, hydroxyl, methoxy, ethoxy, propoxy, isopropoxy, fluoro, chloro, bromo, iodo, and trifluoromethyl.

5. The compound of claim 1, wherein said compound is selected from the group consisting of N-methyl-2R-phenacyl-6S-trans-styrylpiperidine, cis-10R,2S,6R—N-methyl-6-[1-(2-hydroxy-2-phenyl)-ethyl]-2-trans-styrylpiperidine, cis-10S,2S,6R—N-methyl-6-[1-(2hydroxy-2-phenyl)-ethyl]-2-trans-styrylpiperidine, N-methyl-2R-phenacyl-6S-trans-styrylpiperidine, N-Methyl-2R-(2R-hydroxy-2-phenethyl)-6S-trans-styrylpiperidine, N-methyl-2R-(2S-hydroxy-2-phenethyl)-6S-trans-styrylpiperidine, and N-methyl-2R-(2-phenethyl)-6S-trans-styrylpiperidine.

6. A 2,6-substituted piperidino compound or pharmaceutically effective salts thereof, including resolved diasteriomers or enantiomers thereof, comprising the following formula:

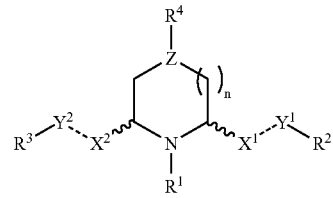

wherein:
n=0, 1, 2, or 3;
X$^1$—Y$^1$ represents a cis-carbon-carbon double bond or a trans-carbon-carbon double bond;
X$^2$ represents CH$_2$;
Y$^2$ represents CHOH or C=O;
Z represents CH;
R$^1$ and R$^4$ are the same or independently different from one another and represent hydrogen or a lower straight chain or branched alkyl;
R$^2$ and R$^3$ are the same or are independently different from one another and represent a saturated or unsaturated hydrocarbon ring, or an ortho, meta or para-substituted benzene.

7. The compound of claim 6, wherein R$^2$ and R$^3$ are benzene rings.

8. The compound of claim 6, wherein R$^1$ is hydrogen, methyl, ethyl or propyl.

9. The compound of claim 6, wherein R$^1$ is hydrogen, methyl, ethyl or propyl.

10. The compound of claim 1, wherein R$^2$ and R$^3$ are substituted benzenes containing at least one substituent selected from the group consisting of methyl, ethyl, propyl, isopropyl, butyl, sec-butyl, isobutyl, carboxaldehyde, acetoxy, propionyloxy, isopropionyloxy, acetyl, propionyl, formyl, benzoyl, hydroxyl, methoxy, ethoxy, propoxy, isopropoxy, fluoro, chloro, bromo, Iodo, and trifluoromethyl.

11. The compound of claim 6, wherein the compound is selected from the group consisting of N-methyl-2R-trans-styryl-6S-(2-phenethyl)piperidine and N-methyl-2S-trans-styryl-6S-(2-phenethyl)piperidine.

12. A 2,6-substituted piperidino or a 2,6-substituted piperazino compound or pharmaceutically effective salts thereof, including resolved diasteriomers or enantiomers thereof, comprising the following formula:

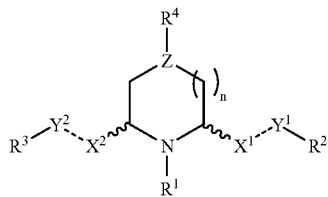

wherein
n is an integer from 0 to 3;
$X^1$—$Y^1$ and $X^2$—$Y^2$ are the same or independently different and represent a $CH_2$—$CH_2$ or $CH_2$—CHOH;
Z-$R^4$ represents N—$R^4$, CH—$R^4$ or C=O, where $R^4$ is hydrogen or a lower straight chain or branched alkyl;
$R^1$ represents hydrogen or a lower straight chain or branched alkyl; or when Z is CH—$R^4$, $R^1$ and $R^4$ together form a ring including a —$CH_2$—, —O—$CH_2$—O—, —$CH_2CH_2$—, —$CH_2CH_2$—$CH_2$—, -cis-CH=CH, -cis-$CH_2$—CH=CH— or -cis-$CH_2$=CH—$CH_2$— moiety;
$R^2$ and $R^3$ are the same or are independently different from one another and represent a saturated or unsaturated hydrocarbon ring, or an ortho, meta or para-substituted benzene.

13. The compound of claim 12, wherein $R^1$ is hydrogen, methyl, ethyl or propyl.

14. The compound of claim 12, wherein $R^2$ and $R^3$ are benzene rings.

15. The compound of claim 12, wherein $R^2$ and $R^3$ are substituted benzenes containing at least one substituent selected from the group consisting of methyl, ethyl, propyl, isopropyl, butyl, sec-butyl, isobutyl, carboxaldehyde, acetoxy, propionyloxy, isopropionyloxy, acetyl, propionyl, formyl, benzoyl, phenyl, hydroxyl, methoxy, ethoxy, propoxy, isopropoxy, fluoro, chloro, bromo, iodo, and trifluoromethyl.

16. The compound of claim 12, wherein $R^2$ and $R^3$ are napthyl or diphenyl groups.

17. The compound of claim 12, wherein Z is N—$R^4$.

18. The compound of claim 12, wherein Z is CH—$R^4$.

19. The compound of claim 1, wherein the compound is cis-1OS,2S,6R—N-methyl-6-[1-(2-hydroxy-2-phenyl)-ethyl]-2-trans-styrylpiperidine.

* * * * *